(12) United States Patent
Min et al.

(10) Patent No.: US 8,568,355 B2
(45) Date of Patent: Oct. 29, 2013

(54) AGENT DELIVERY CATHETER HAVING A RADIALLY EXPANDABLE CENTERING SUPPORT MEMBER

(75) Inventors: Sung Woo Min, Mountain View, CA (US); Randolf von Oepen, Los Altos, CA (US); Binh T. Nguyen, Newark, CA (US); Kevin J. Ehrenreich, San Francisco, CA (US); William E. Webler, Jr., San Jose, CA (US); Rommel Lumauig, San Jose, CA (US); Gregory W. Chan, San Francisco, CA (US); Lorcan J. Coffey, Tubingen (DE); Travis R. Yribarren, Campbell, CA (US); Jesus Magana, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/323,122

(22) Filed: Dec. 12, 2011

(65) Prior Publication Data

US 2012/0143139 A1 Jun. 7, 2012

Related U.S. Application Data

(62) Division of application No. 12/328,390, filed on Dec. 4, 2008, now Pat. No. 8,075,519.

(60) Provisional application No. 60/992,983, filed on Dec. 6, 2007.

(51) Int. Cl.
*A61M 29/00* (2006.01)
*A61M 5/178* (2006.01)

(52) U.S. Cl.
USPC ............... 604/104; 604/164.01; 604/164.03

(58) Field of Classification Search
USPC ............... 604/96.01, 103, 103.01, 103.03, 604/103.06, 103.07, 103.11–103.14, 604/104–107, 164.01, 164.03
See application file for complete search history.

(56) References Cited

U.S. PATENT DOCUMENTS

| 4,762,130 A | 8/1988 | Fogarty et al. |
| 5,464,395 A | 11/1995 | Faxon et al. |

(Continued)

FOREIGN PATENT DOCUMENTS

| DE | 102006003181 A1 | 7/2007 |
| EP | 0810004 A | 12/1997 |

(Continued)

OTHER PUBLICATIONS

International Search Report issued Mar. 4, 2009, pp. 1-5.

(Continued)

*Primary Examiner* — Nicholas Lucchesi
*Assistant Examiner* — Leah Stohr
(74) *Attorney, Agent, or Firm* — Fulwider Patton LLP

(57) ABSTRACT

A catheter for delivering an agent to an injection site in a wall of a patient's body lumen, with an elongated shaft having a needle-through lumen slidably containing a needle therein, and an expandable member on the distal shaft section which has a collapsed configuration and a radially expanded configuration. In the radially expanded configuration, the expandable member supports the shaft in a position spaced away from the body lumen wall, and the needle slidably exits the needle-through lumen in the extended configuration through the port spaced away from the body lumen wall as a portion of the expandable member maintains the position of the port section of the shaft in the body lumen. The expandable member typically has an open-walled, helical, or lobed configuration providing a perfusion path along the expandable member.

10 Claims, 12 Drawing Sheets

(56) References Cited

U.S. PATENT DOCUMENTS

| | | | |
|---|---|---|---|
| 6,159,139 A * | 12/2000 | Chiu | 600/3 |
| 6,450,988 B1 | 9/2002 | Bradshaw | |
| 6,458,098 B1 | 10/2002 | Kanesaka | |
| 6,554,801 B1 | 4/2003 | Steward et al. | |
| 2002/0072706 A1 | 6/2002 | Hiblar et al. | |
| 2004/0118415 A1 | 6/2004 | Hall et al. | |
| 2005/0203462 A1 | 9/2005 | Katoh et al. | |
| 2006/0106338 A1 * | 5/2006 | Chang | 604/104 |

FOREIGN PATENT DOCUMENTS

| | | |
|---|---|---|
| WO | 9404220 A | 3/1994 |
| WO | 9526776 A | 10/1995 |
| WO | 2006055826 A2 | 5/2006 |

OTHER PUBLICATIONS

Japanese Office Action of Mar. 5, 2013.

* cited by examiner

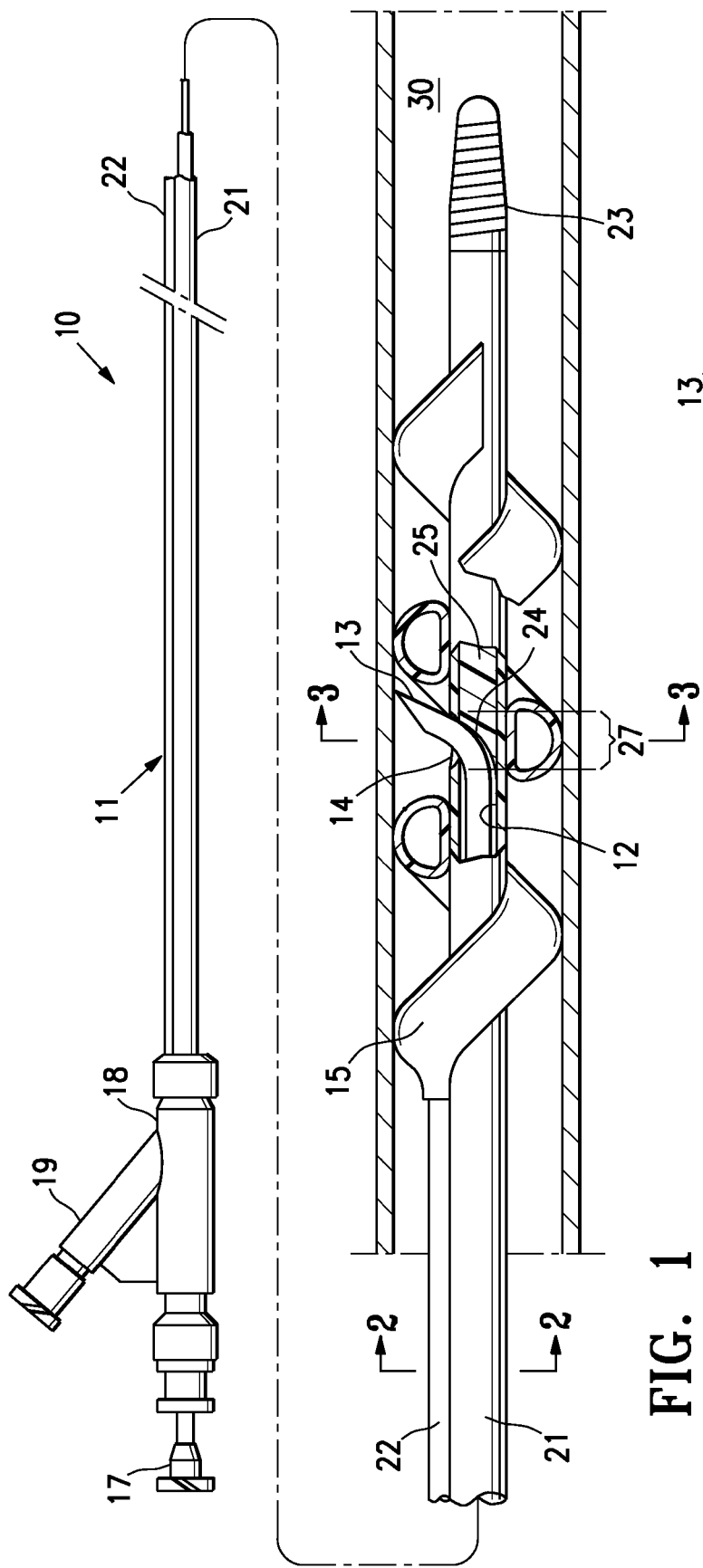
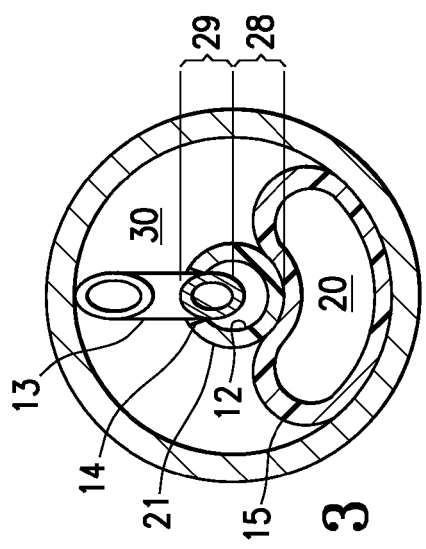
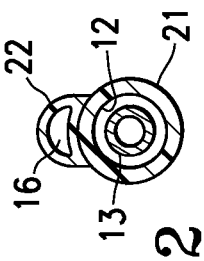
FIG. 1
FIG. 3
FIG. 2

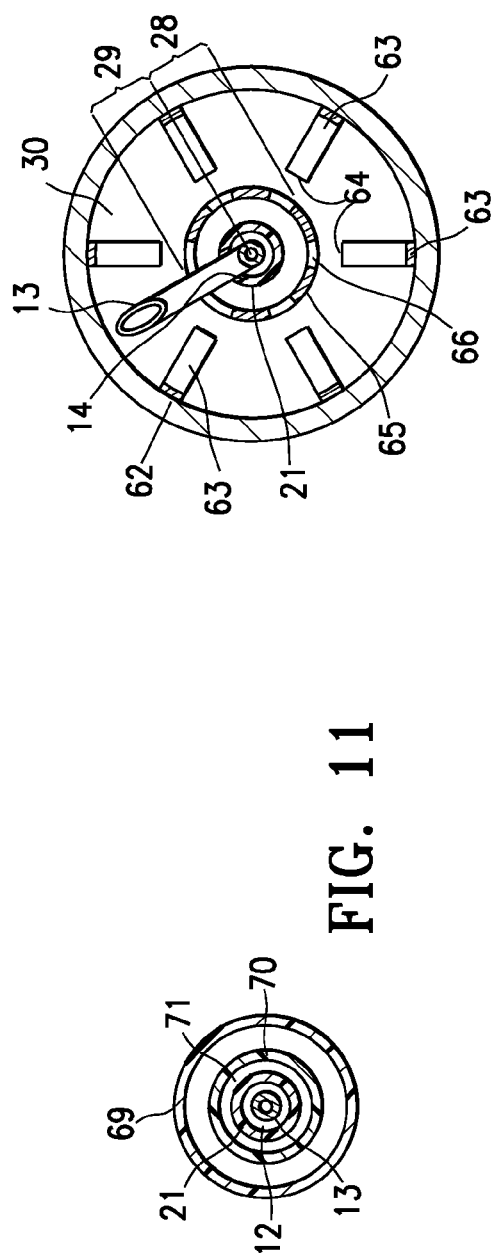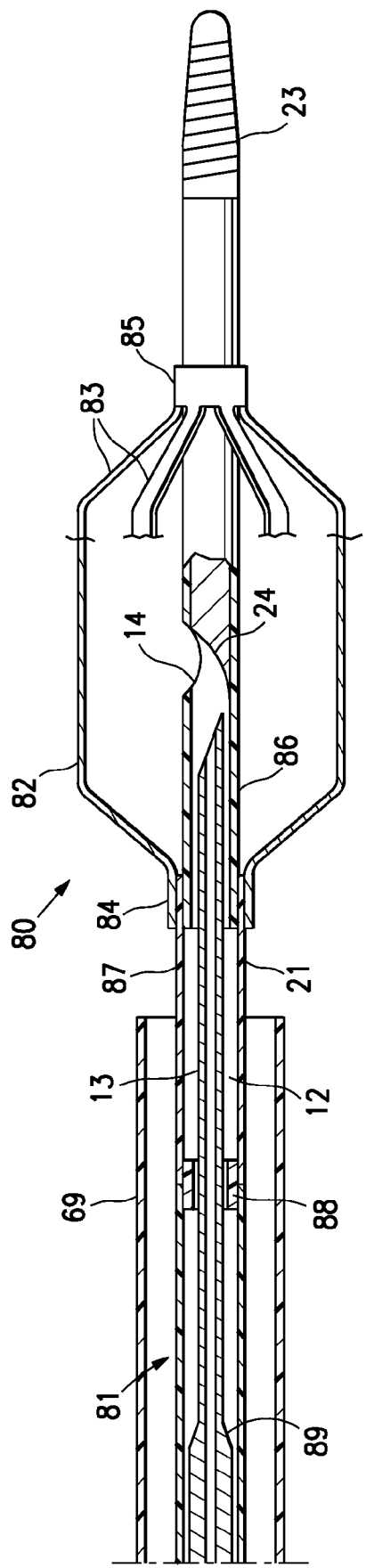

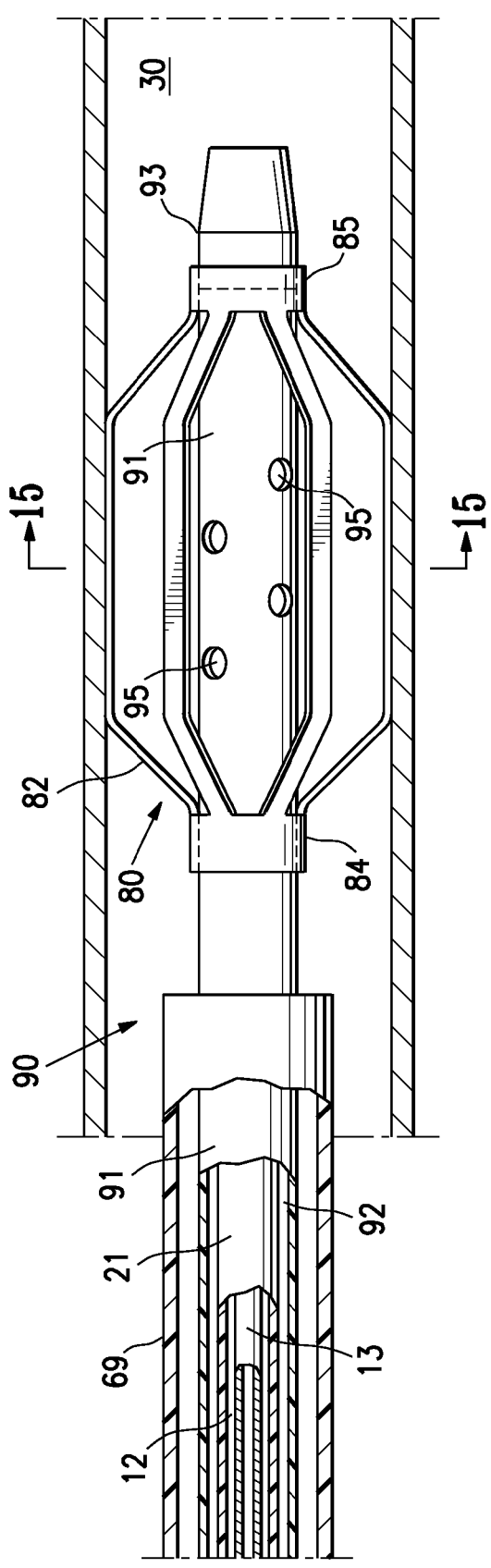
FIG. 14
FIG. 15
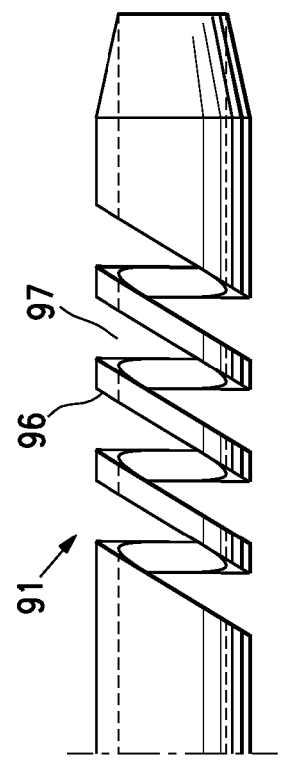
FIG. 16

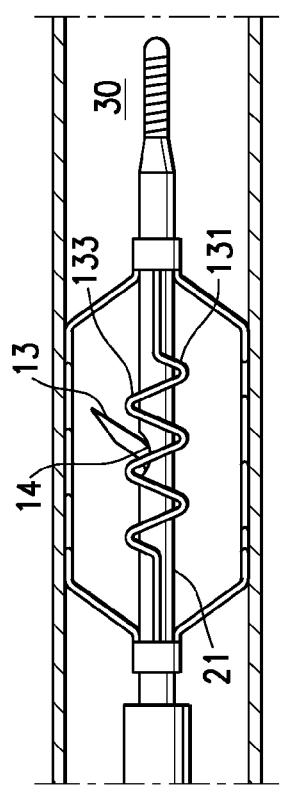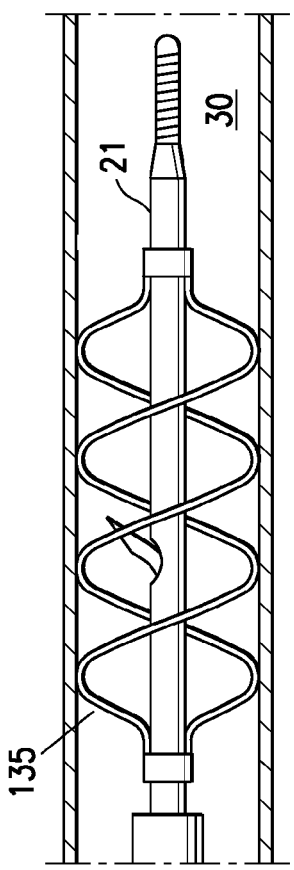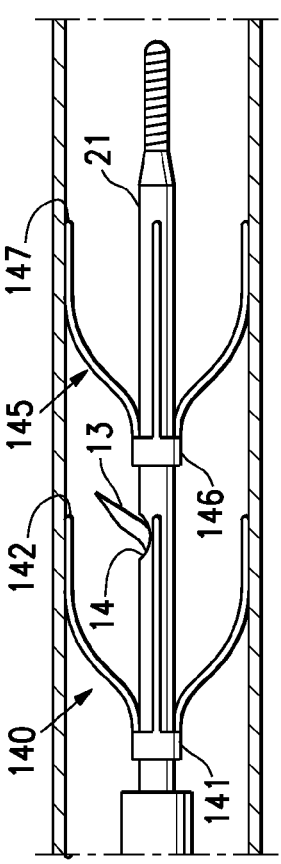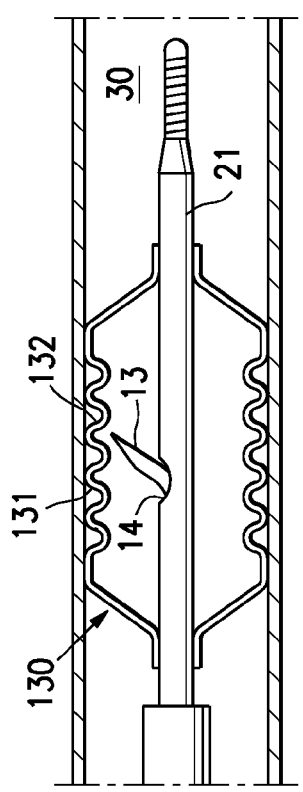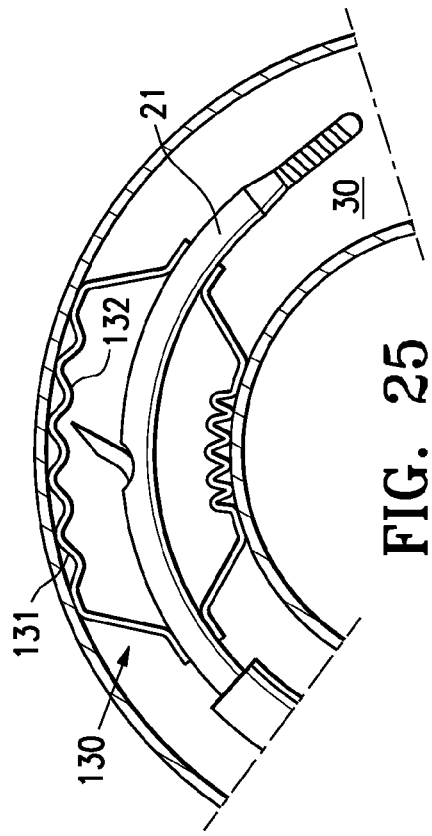

AGENT DELIVERY CATHETER HAVING A RADIALLY EXPANDABLE CENTERING SUPPORT MEMBER

CROSS-REFERENCES TO RELATED APPLICATIONS

This Divisional Application is based on U.S. Ser. No. 12/328,390, filed on Dec. 4, 2008 now U.S. Pat. No. 8,075,519, issuing on Dec. 13, 2011; which claims priority to U.S. provisional application No. 60/992,983, filed Dec. 6, 2007.

BACKGROUND OF THE INVENTION

The invention relates to the field of medical devices, and more particularly to catheters, such as needle catheters or other elongated devices configured for inserting into a patient's body lumen to perform diagnostic or therapeutic procedures including the delivery of an agent to the coronary or peripheral vasculature.

The delivery of therapeutic agents into various parts of the vascular system has been shown to be an effective method of treating vascular disease. A variety of agents can be delivered including anti-proliferative, anti-inflammatory, anti-neoplastic, anti-platelet, anti-coagulant, anti-fibrin, anti-thrombotic, anti-mitotic, antibiotic, anti-allergic, and antioxidant compounds. To treat a diseased section of the vessel, these agents could be delivered directly into the vessel wall adjacent to the diseased section, and/or into the perivascular space. Vascular regenerative therapies, such as the delivery of mesenchymal stem cells, require the delivery of a bolus of biologic materials into a portion of the vascular system such as into the tissue surrounding a coronary vessel. Local, as opposed to systemic delivery is a preferred method of treatment in that smaller total levels of medication are administered in comparison to systemic dosages yet are concentrated at a specific site. As a result, local delivery produces fewer side effects and achieves more effective results.

A variety of methods and devices have been proposed for percutaneous drug delivery to a diseased region of the vasculature, including catheters having a needle configured to be directed out of the catheter and into the vessel wall to deliver the desired agent to the tissue. In order to properly position the distal end of a drug delivery catheter in a patient's tortuous distal vasculature, the catheter should preferably have a low-profile, flexible distal section despite also having the necessary structural components required for the drug delivery at the operative distal end of the catheter. One difficulty has been accurately puncturing the vessel wall at a specific desired location, for effective, accurate delivery of an agent into the vessel wall from a catheter located within the vessel.

SUMMARY OF THE INVENTION

The invention is directed to a catheter configured for delivering an agent to an injection site in a wall of a patient's body lumen, with an expandable support member which greatly facilitates accurately delivering an agent to the desired injection site.

A catheter of the invention generally includes an elongated shaft having a proximal end, a distal end, a needle-through lumen slidably containing a needle therein, and at least one needle-through port in a side of a distal shaft section for lateral egress of the needle such that the needle has a retracted and an extended configuration, and an expandable member on the distal shaft section which has a collapsed configuration and a radially expanded configuration. In the radially expanded configuration, the expandable member supports the shaft in a position spaced away from the body lumen wall, and the needle slidably exits the needle-through lumen in the extended configuration through the port spaced away from the body lumen wall as a portion of the expandable member maintains the position of the port section of the shaft (i.e., the length of the shaft through which the needle exits the catheter shaft) in the body lumen. In presently preferred embodiments, the expandable member is configured to provide for perfusion of fluid in the patient's body lumen (i.e., allow blood within the body lumen to flow past the expandable member in the expanded configuration). The expandable member typically has an open-walled, helical, or lobed configuration providing the perfusion path along the expandable member.

The expandable member generally includes a portion which is at the radial location of the port on the side of the shaft opposite to the port-side of the shaft, and which expands into contact with the body lumen wall. The expandable member preferably also has at least a section which extends fully around the circumference and along an outer surface of the shaft, to substantially center the port section of the shaft in the body lumen in the expanded configuration.

In accordance with the invention, by providing support to the shaft at a location substantially opposite to the port, the expandable member preferably prevents or inhibits the tendency of the catheter body to be forced away from the injection site as the needle contacts and is forced into the vessel wall during an agent delivery procedure. Specifically, when the needle contacts the vessel wall, it creates a reactive load on the catheter body, which can otherwise force the catheter shaft away from the vessel wall and make it more difficult to puncture the vessel. This reaction and resultant movement of the catheter shaft can contribute to several problems. For example, it may cause "tenting" or the billowing of the vessel wall which may lead to inaccurate penetration depths of the needle and inaccurate needle location in the longitudinal or radial location. Further, the physician may overcompensate for this, which could cause a perforation if the needle is advanced with too much force. Thus, the portion of the expandable member which is at the radial location of the port but opposite to the port-side of the shaft will counter this reactive force caused by the advancement of the needle, and thereby maintain the position of the distal shaft section in the patient's vessel. One aspect of the invention is directed to an expandable member that provides a varying level of support throughout the expandable structure, which in one embodiment is configured to provide maximum support substantially opposite to the injection site. Another aspect of the invention is directed to a catheter having a rotational alignment feature configured to maintain the needle in a rotational alignment relative to the shaft when the needle is in the retracted or the extended configuration.

A catheter of the invention is configured for being percutaneously tracked within the patient's body lumen to a desired treatment site in a method of delivering an agent at the treatment site. Once at the treatment site, the expandable member is expanded to support the catheter in a desired position in the patient's body lumen during advancement of the needle into the target tissue, such that the catheter of the invention provides for improved ease of use and effective, accurate delivery of an agent to a desired location in the patient. The expandable member preferably substantially centers the catheter shaft in the patient's body lumen so that the needle exits the shaft and ramps to the body lumen wall at a desired attack angle, while also supporting the catheter at a location opposite to the needle-through port so that the catheter shaft is not forced away from the injection site as the needle contacts and enters the wall of the patient's body lumen. These and other advantages of the invention will become more apparent from the following detailed description of the invention and accompanying exemplary drawings.

BRIEF DESCRIPTION OF THE DRAWINGS

FIG. 1 is an elevational, partially in section, view of an agent delivery perfusion catheter embodying features of the invention, having a helically extending expandable balloon member in an inflated configuration within a patient's body lumen.

FIGS. 2 and 3 are transverse cross sections of FIG. 1, taken along lines 2-2 and 3-3, respectively.

FIGS. 11 and 12 are transverse cross sections of FIG. 10, taken along lines 11-11 and 12-12, respectively.

FIG. 13 illustrates an alternative embodiment in which the open-walled frame has expandable struts extending from a proximal skirt section to a distal skirt section, and the open-walled frame is mounted on the needle sheath tubular member of the shaft FIG. 14 illustrates an alternative embodiment in which the frame skirt sections are mounted on an outer surface of a tubular member of the shaft which has a lumen configured to slidably received the shaft needle sheath tubular member and which has a wall defining multiple needle-through openings.

FIG. 15 is a transverse cross section of FIG. 14, taken along line 15-15.

FIG. 16 illustrates an alternative embodiment of the distal section of the shaft tubular member having a spiral slotted wall defining multiple needle-through openings.

FIG. 24 illustrates a longitudinal sectional view of a distal shaft section of an alternative embodiment in which the frame struts have a curvilinear portion configured to compress or elongate.

FIG. 25 illustrates the catheter of FIG. 24 in a curved section of the patient's body lumen.

FIG. 26 illustrates an elevational view of an alternative embodiment in which the curvilinear portion has undulations which turn in a plane substantially parallel to the longitudinal axis of the frame.

FIG. 27 illustrates an elevational view of a distal shaft section of an alternative embodiment in which the frame struts configured to compress or elongate are helically extending around the shaft.

FIG. 28 illustrates an elevational view of an alternative embodiment configured to adjust to the vessel anatomy, having two axially spaced frames with free distal ends.

DETAILED DESCRIPTION OF THE PREFERRED EMBODIMENTS

Figure 4:
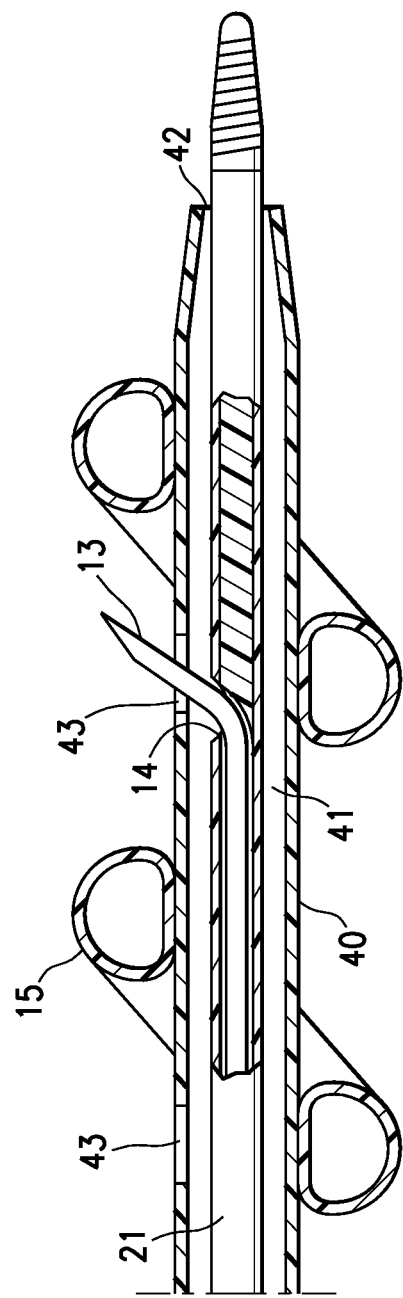
FIG. 4 illustrates an alternative embodiment, partially in section, of the catheter distal shaft section, in which the balloon spirals along an outer surface of a tubular member of the shaft which has a lumen configured to slidably received the shaft needle sheath tubular member.

FIG. 1 illustrates an elevational, partially in section, view of an agent delivery perfusion catheter 10 embodying features of the invention, generally comprising an elongated catheter shaft 11 having a proximal end, a distal end, a needle-through lumen 12 slidably containing a hollow needle 13 therein, and at least one needle-through port 14 in a side of a distal shaft section for lateral egress of the needle 13, and an expandable member 15 on the distal shaft section. The catheter 10 is illustrated in FIG. 1 in a patient's body lumen 30, with the expandable member 15 expanded and the needle 13 at least partially extended. The catheter 10 is configured to be introduced into the patient's vasculature and advanced percutaneously in a low profile configuration (not shown), with the expandable member 15 in a collapsed configuration and the needle 13 distal end in a retracted configuration within the shaft 11, to position the port 14 at a desired location. The expandable member is then expanded to the expanded configuration as illustrated in FIG. 1, and the needle distal end slidably advanced out the port 14 and into the vessel wall, and agent delivered from the needle to the tissue (e.g., into the vessel wall and/or perivascular space). The needle tip extends radially beyond the outer profile of the expandable member in the expanded configuration, although the catheter is typically configured to allow the needle to extend only a set limited distance away from the shaft, as for example providing a needle stop such as is discussed in more detail below. A proximal handle 17 at the proximal end of the needle 13 is configured for attaching to an agent source (not shown) to flow agent through the lumen of the needle 13 to the piercing distal tip of the needle 13. A proximal adapter assembly 18 secured to the shaft proximal end provides access to the needle-through lumen 12, and, in the embodiment of FIG. 1, has a Y-arm adapter with a sidearm port 19 configured for attaching an inflation fluid source (not shown) into fluid communication with an inflation lumen 16 of the shaft for inflating expandable member 15. In embodiments in which a distal end section of the needle is biased to assume a bend or curved shape when extended from the catheter, a proximal handle may be configured to control the rotational orientation of the needle 13 to improve the ease and reliability with which the needle is extended out the port 14. For example, a distal portion of a needle handle can be configured to longitudinally slidably interface with adapter 18 to prevent the uncontrolled rotation of the handle and thus needle 13 as well. Additionally, the handle and adapter 18 may also be configured to control needle extension and retraction, provide limits to the proximal and distal motion of the needle 13 relative to the needle sheath tubular member 21, and optionally prevent their separation. In some embodiments, the proximal adapter 18 is configured to contain a second sidearm that communicates with the needle-through lumen 12 to allow the flushing out of lumen 12 (i.e., out of the annular space between the outer diameter of the needle 13 and inner diameter of the shaft therearound) with a solution, e.g., heparinized solution, to prevent emboli and blood clotting in lumen 12 which could otherwise prevent needle 13 extension or retraction.

The shaft 11 comprises a needle sheath tubular member 21 defining the needle-through lumen 12 and port 14 of the shaft. In the embodiment of FIG. 1, the inflation lumen 16 is defined by an outer tubular member 22 extending eccentrically along an outer surface of the needle sheath tubular member 21 and needle-through lumen 12 therein, as best shown in FIG. 2 illustrating a transverse cross sectional view of the catheter of FIG. 1, taken along line 2-2. However, the inflation lumen 16 can be provided by a variety of suitable shaft designs including coaxial lumen or coextruded dual-lumen designs, as for example when the inflation lumen 16 is at least partially within or defined by a wall of the needle sheath tubular member 21. The outer tubular member 22 extends distally to a location proximally spaced from the distal end of the catheter shaft, and a distal end of the outer tubular member 22 is sealingly secured to a proximal end of the expandable member 15, such that the inflation lumen 16 is in fluid communication with an inflatable interior 20 of the balloon (see FIG. 3, illustrating a transverse cross sectional view of the catheter of FIG. 1, taken along line 3-3), for inflation/deflation of the expandable member 15 in the embodiment of FIG. 1. Specifically, a coaxial lumen design (with the inflation lumen being an annular space between coaxial tubes) facilitates control over the catheter's rotational orientation as the catheter is rotated, and provides for relatively fast inflation/deflation. In one embodiment, the outer surface of the proximal end of the expandable member 15 is sealingly secured to the inner surface of the outer tubular member 22. In one embodiment, the outer tubular member 22 spirals around the needle sheath tubular member 21, for at least some distance proximally (preferably about 30 cm or more) from its seal at the proximal end of the expandable member 15 to provide improved torque (rotational orientation) control to the elongated catheter shaft 11 in the patient's tortuous vascular anatomy.

The needle sheath tubular member 21 typically includes a closed distal end and a flexible distal tip member 25 having a coiled wire tip 23 configured to facilitate atraumatically advancing the catheter 10 through the patient's body lumen 30, and selecting the desired branches of the vascular tree during catheter positioning. The catheter 10 of the embodiment of FIG. 1 is thus a fixed wire-type device, although a catheter of the invention can alternatively be configured to slidably receive a guidewire in a lumen of the shaft (over-the-wire) for tracking through the patient's vasculature, as discussed in more detail below. The fixed wire tip can use a variety of suitable conventional guidewire-like constructions, and a polymer jacket and/or coating may be applied to the fixed-wire tip. The member 25/coiled tip 23 may be formed with a bend or later bent by the user prior to insertion to facilitate the ability of the member 25 to select a branch as the catheter is rotated and then advanced, such that the bent distal end of member 25 engages the lumen wall of the desired vessel branch. A ramp 24 in the needle sheath tubular member 21 distally adjacent to the port 14 occludes the needle-through lumen and facilitates guiding the needle 13 laterally through the side wall of the shaft 11. The ramp 24 in the illustrated embodiment is formed by a proximal end of the flexible distal tip member 25 which has a distal end secured to the flexible distal tip coil 23 of the catheter, although it could alternatively be provided by a beveled member proximal to the flexible distal tip member 25. The needle distal section extending through the port 14 and outside of the shaft 11 is preferably oriented at an angle relative to a transverse plane perpendicular to the longitudinal axis of the shaft 11, although the catheter and needle can alternatively be configured so that the angle of the extended needle distal section is substantially perpendicular to the axis of the shaft if desired. Depending on factors such as the preset bend angle, radius of curvature and/or angle of curvature, if any, in the distal section of the needle, the catheter facilitates controlling the attack angle of the needle by design as it extends toward the wall of the body lumen 30. In one presently preferred embodiment, the attack angle of the needle does not exceed 90 degrees (relative to the longitudinal axis of the shaft at the shaft distal tip), due to the resulting difficulty in the mechanical configuration of the ramp and port, and due to the tendency of the needle to bend or deform when it contacts the vessel wall rather than penetrate directly into the vessel wall at attack angles of greater than 90 degrees. The beginning needle angle of attack is primarily determined by the configuration of ramp 24 and the port 14. If the needle has no curvature or bend preset into its distal end, the needle angle of attack remains relatively constant during needle extension. If the needle has a bend/curvature preset into its distal end, the needle angle of attack changes as its preset bent/curved section engages ramp 24 and port 14 until that section of the needle has exited port 14. In some embodiments, applying at least some amount of curvature over at least a short portion of the distal end of the needle is desirable in order to assure that the needle will easily exit the port 14.

FIG. 4 illustrates an alternative embodiment in which the shaft 11 further comprises an inner tubular member 40 having a lumen 41 which is configured to slidably receive the shaft needle sheath tubular member 21 and which extends to a distal tip port 42 in the distal end of the inner tubular member 40. In FIG. 4, the inner tubular member 40 and expandable member 15 are illustrated in cross section, to facilitate illustration of the needle sheath tubular member 21 therein, and the needle 13 is shown at least partially extended through the needle-through port 14 in the needle sheath tubular member 21. The needle sheath tubular member 21 can be used as a guidewire for advancing the catheter 10 within the patient's vasculature, and/or a separate guidewire (not shown) can be used for tracking the catheter to the desired location within the patient's vasculature and then exchanged for the needle sheath tubular member 21 by proximally sliding the guidewire out of inner tubular member lumen 41 and then distally advancing the needle sheath tubular member 21 into the inner tubular member as illustrated in FIG. 4. In the embodiment of FIG. 4, the inner tubular member 40 has multiple side wall ports 43 configured to allow for lateral egress of the needle 13 as the needle exits the needle-through port 14 in the side wall of the needle sheath tubular member 21. In the embodiment of FIG. 4, the shaft inflation lumen (not shown in FIG. 4) in fluid communication with the expandable member 15 can be provided by an outer tubular member extending eccentric or coaxial to lumen 41 outside of the inner tubular member 40, or by a second lumen defined within a wall of the inner tubular member 40. The lumen 41 of the inner tubular member 40 can be configured as a rapid exchange and/or a full length over-the-wire lumen, although a full length lumen 41 is preferred for exchanging a separate guidewire for the needle 13/needle sheath tubular member 21. In a rapid exchange design, a proximal rapid exchange wire port (not shown) in the side wall of the inner member 40, spaced distally from the proximal end of the shaft, allows for a guidewire and/or the needle sheath tubular member 21 to extend within a relatively short length of the lumen 41 between the proximal rapid exchange port and the distal port 42 so that the proximal length of the wire outside of the patient's body can be grasped by the physician when inserting or removing the catheter from the body to hold the guidewire in position in the vasculature. The proximal rapid exchange port, if provided, is preferably proximally spaced from the proximal end of the expandable member 15. The distal end of the inner tubular member 40 is an atraumatic distal tip. A variety of suitable distal tip configurations can be used, typically involving a lower durometer polymeric member secured to the end of the inner tubular member, or alternatively formed as an integral one-piece unit by the end of the inner tubular member 40. Flexibility enhancing features may also be integrated within the distal tip design, such as spiral cuts, annealing processes, and the like.

The expandable member 15 extends around the circumference and along an outer surface of the shaft 11 (i.e., on the outer surface of a distal section of the needle sheath tubular member 21 in the embodiment of FIG. 1, and on the outer surface of a distal section of the inner tubular member 40 in the embodiment of FIG. 4) to substantially center the shaft at port 14 in the body lumen 30 in the expanded configuration, and has a portion 27 at the radial location of the port 14 on the shaft side 28 opposite to the port-side 29 (see FIG. 3) of the shaft 11, expanded into contact with the body lumen wall in the expanded configuration. The expandable member 15 in the expanded configuration supports the shaft 11 in a position spaced away from the body lumen wall around the circumference of the shaft at the location of the port 14 (i.e., the part of the shaft defining the port 14 is radially spaced inwardly from the body lumen wall), and the needle 13 slidably exits the needle-through lumen 12 in the extended configuration through the port 14 spaced away from the body lumen wall as the expandable member supports the shaft at the port 14. Thus, as the needle 13 is extended into contact with an injection site on the wall of the body lumen 30, the shaft is supported and flexing in the opposite direction away from the injection site despite the reactive force that the needle applies to the needle sheath tubular member 21 is minimized and/or controlled. In contrast, if the reactive force of the needle was allowed to cause disadvantageous catheter flexing as the needle is forced into the tissue, it can result in sub-optimal accuracy of needle penetration depth control by the physician. Additionally, because the expandable member 15 substantially centers the port 14 in the body lumen 30 such that the port 14 is spaced a distance away from the body lumen wall injection site, and typically by a distance of less than one half the lumen 30 diameter, the catheter 10 facilitates providing an optimum attack angle by design for the needle 13 as it is extended toward the body lumen wall (e.g., by reducing the range of needle extension lengths and amount of needle extension that must be accommodated, relative to the range and length required of a design without the expandable member centering). Some irregularity in a patient's vasculature is to be expected, such that the terminology "substantially centered" should be understood to include positions in which the shaft 11 at the port 14 is somewhat closer to one side of the vessel wall than to another due to the section of the body lumen 30 being irregular and/or curved. However, it should be understood that the section of the shaft having the needle-through port 14 will be spaced away from the body lumen wall around the circumference thereof by the expandable member 15 in the expanded configuration, and the expandable member is configured such that in a straight section of a body lumen 30 the shaft at the port 14 will be positioned at about the center of the body lumen 30.

In the embodiment of FIG. 1, the expandable member 15 is a helically extending balloon with the shaft needle-through port 14 located between helical turns of the balloon. As a result, the helical balloon 15 allows for perfusion of fluid within the body lumen 30 along a helical perfusion channel defined in the body lumen 30 along the outer surface of the helical balloon 15 (and underlying section of the shaft) inflated into contact with the body lumen wall. By allowing blood flow perfusion during an injection procedure, the catheter 10 of the invention facilitates the safe and effective delivery of agent to one or more treatment sites over the optimum, and potentially extended, time span required for the treatment. Additionally, the helical balloon is preferably mounted to the shaft at a position relative to the port 14 such that it expands into contact with the body lumen wall at a location approximately opposite to the port 14 and needle 13 exiting the port 14 in the extended configuration, to maintain the shaft radial position in the body lumen during extension and retraction of the needle 13 into and out of the wall of the body lumen 30. The proximal end of the helical balloon 15 is sealingly secured, as for example by heat fusion or adhesive bonding, to the shaft such that the balloon is in fluid communication with the inflation lumen 16, for inflation/deflation of the balloon 15. Additionally, at least the distal end of the helical balloon is bonded to the outer surface of the shaft needle sheath tubular member 21. All or part of the length of helically extending central section of the balloon 15, between the proximal and distal bonded ends of the balloon, can be free or similarly bonded to the underlying section of the shaft 11. In one presently preferred embodiment, the entire length is bonded to ensure that the balloon position on the shaft does not shift during advancement of the catheter in the body lumen, such that the balloon remains clear of the port and will not be punctured by the extending needle and to ensure that the balloon provides the desired support to the shaft opposite to the port. In an alternative embodiment, the helically extending central length of the balloon is bonded to the shaft just at the positions where the balloon is adjacent to and opposite to the port 14. The terminology "helically" as used herein should be understood to refer generally to a spiraling, coil or spring-like configuration, as opposed to an axially aligned member which extends substantially straight (e.g., with no intentionally induced spiraling or curving around the catheter longitudinal axis). In an alternative embodiment, the balloon has a wave-like rather than a helical shape.

Figure 5:
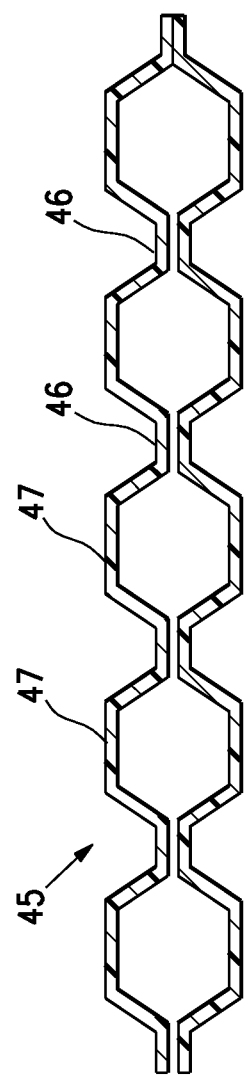
FIG. 5 is a longitudinal cross sectional view of a segmented balloon, partially in section, which in one embodiment forms the helical balloon.

The helical balloon 15 can be formed of a variety of conventional polymeric materials used in catheter balloon construction, including polyamides such as nylon and polyether block amide (PEBAX) copolyamides, polyurethanes, polyethyleneterephthalate (PET), and the like. In one embodiment, the helical balloon is formed by blow-molding a tubular parison in spiral balloon mold to produce a helical balloon, such that the forces applied to the shaft by the balloon during its inflation are minimized (e.g., forces that might cause a flexible distal shaft section to deform into a spiral). The spiral balloon mold has a proximal tapered section configured to provide the proximal end of the balloon with a diameter close to that of the catheter shaft section that will be sealingly secured to the balloon proximal end, and the helical balloon distal end is similarly tapered by the mold and may be closed as a part of the balloon blowing process or as a secondary process. In an alternative embodiment, the helical balloon 15 is formed of a tubular balloon having proximal and distal skirt sections, and inflatable tapered sections on either end of a generally uniform cylindrical inflatable length, as is commonly used for balloon catheter dilatation balloons, except that the tubular balloon distal end is closed together to itself, and the balloon is helically wrapped around the distal shaft section. To minimize a tight, sharp twist or fold in the balloon caused by forcing the uniform cylindrically shaped working length to spiral along the shaft, such a balloon is preferably formed of a relatively soft polymer such as a urethane or silicone based polymer. FIG. 5 illustrates an alternative embodiment in which the helical balloon is formed by a segmented balloon 45 having a series of alternating reduced diameter inflatable sections 46 and larger diameter inflatable sections 47, and the larger diameter sections 47 inflate to a diameter which is larger than the reduced diameter sections and which contacts the patient's body lumen wall. As the segmented balloon 45 is forced to spiral around the shaft 11, the change in diameter of the balloon body results in a strain relief in the small profile areas, which avoids the problems with forcing a uniform cylindrical working length to spiral around the shaft. This reduces the risk of trauma to the vessel by avoiding forming sharp edges along the balloon, and also provides for improved, more uniform centering of the shaft compared to a kinked balloon. In one embodiment, each larger diameter section 47 has a length which extends not more than one revolution around the shaft, and more preferably about one half a revolution around the shaft, so that each 360 degree helical turn of the balloon includes at least part of a reduced diameter section 46 in order to provide the desired strain relief. The length of each larger diameter section 47 is typically about equal to or longer than that of the reduced diameter section 46. As illustrated in FIG. 5, the distal end of the balloon 45 is closed together to itself, prior to mounting the balloon helically along the catheter shaft 11.

Figure 6:
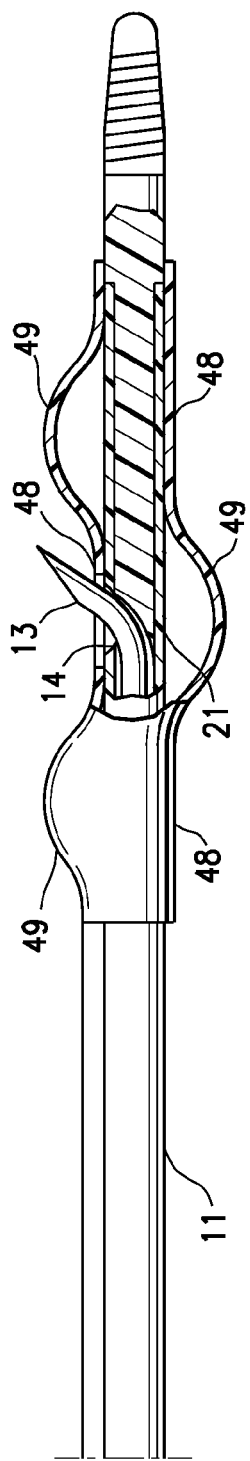
FIG. 6 illustrates an alternative embodiment in which the helical balloon is coaxially mounted on the shaft.

FIG. 6 illustrates an alternative embodiment in which the helical balloon 15 is a tube circumferentially located along the shaft 11 which has a continuous wall extending fully around the circumference of the shaft in a plane perpendicular to the shaft longitudinal axis. Between the proximal and distal skirt sections sealingly secured to the shaft, the tube is bonded to an underlying section of the shaft along a spiral path 48 adjacent to an inflatable (i.e., nonbonded) helical section 49, thereby forming the helical balloon. Unlike the distal end of the helical balloon 15 of the embodiment of FIG. 1, the distal skirt section of the helical balloon 15 of FIG. 6 is coaxially sealingly secured around the circumference of the shaft 11. The needle-through port 14 is formed through the wall of the balloon and shaft, in an area along the bonded spiral path 48 where the balloon 15 is bonded to the underlying section of the shaft (i.e., needle sheath tubular member 21). The circumferential configuration of the balloon provides certain manufacturing and performance advantages.

Figure 7:
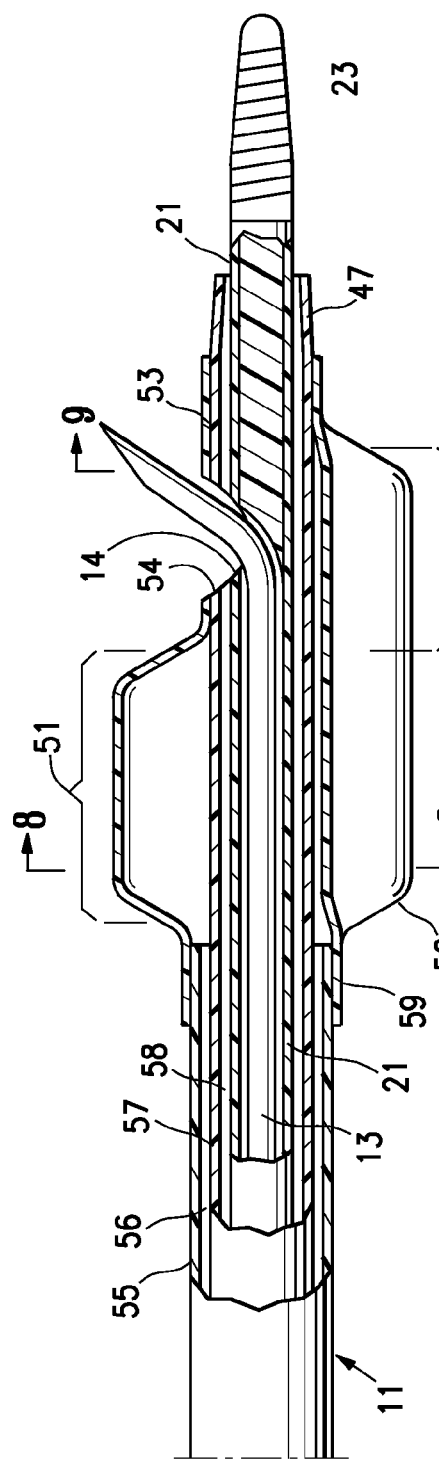
FIG. 7 illustrates an alternative embodiment in which the expandable member is a variable shaped balloon having a lobed section and an eccentric section.
Figure 9:
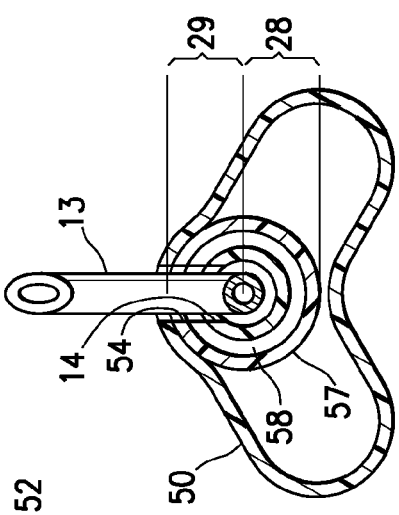
FIGS. 8 and 9 are transverse cross sections of FIG. 7, taken along lines 8-8 and 9-9, respectively.

FIG. 7 illustrates an alternative embodiment in which the expandable member 15 is a variable shaped balloon 50 having a first (e.g. proximal) section 51 longitudinally spaced from (e.g., proximal to) a shaft needle port 54 and that radially expands coaxially around the circumference of the shaft 11, and an eccentric section 52 that expands laterally away from the needle-through port 14 in the needle sheath tubular member 21 (see FIG. 9) and port 54 (which thereby functions in part as the catheter needle-through port) on the side 28 of the shaft opposite to the port-side 29 (see FIG. 9). Thus, the eccentric section 52 is the portion of the expandable member 51 at the radial location of the needle-through port 54 on the shaft side 28 opposite to the port-side 29 of the shaft 11, and the first section 51 substantially centers the shaft at the port 54 in the body lumen 30 in the expanded configuration. Although illustrated with the first section 51 being a proximal section of the balloon and the eccentric section 52 being a distal section of the balloon, it should be understood that the eccentric section at the port 54 could alternatively be a proximal section of the variable shaped balloon 50. Similar to the embodiment of FIG. 6, the balloon is a tube that extends circumferentially around the shaft (i.e., it has a continuous wall extending fully around the circumference of the shaft in a plane perpendicular to the shaft longitudinal axis). Because the tubular wall of the balloon 50 extends circumferentially around the shaft, it has a section 53 sealed to the underlying shaft in order to permit the exit port to be formed for extending and retracting the needle 13 through the catheter shaft needle-through port 54.

Figure 8:
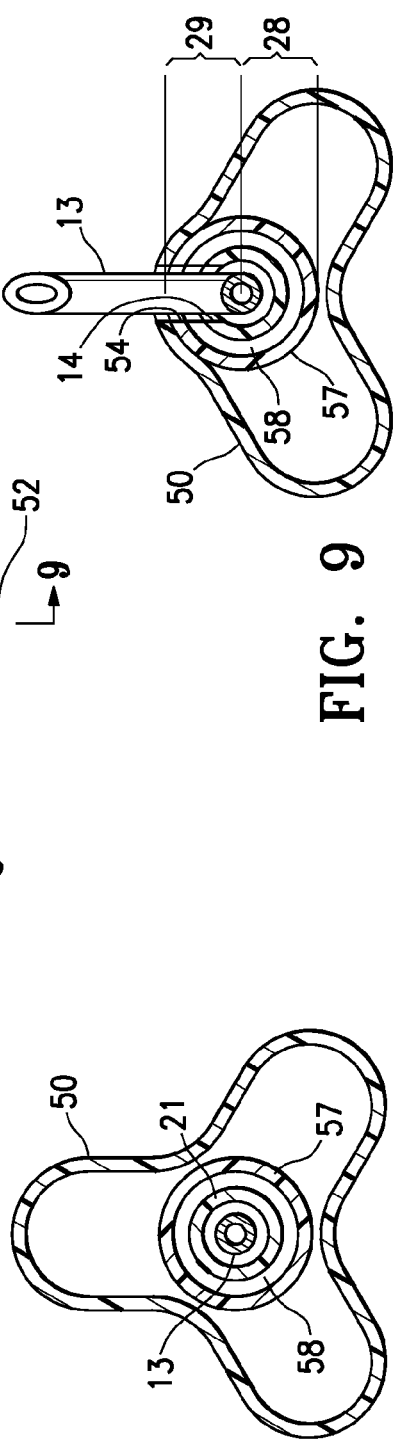

In a presently preferred embodiment, the balloon 50 is a lobed balloon having a radially expanded configuration providing one or more perfusion pathways along an outer surface of the expanded balloon. As best shown in FIGS. 8 and 9, illustrating transverse cross sections of the catheter of FIG. 7, taken along lines 8-8 and 9-9, the lobed balloon 50 has three lobes with three smaller outer diameter wall sections therebetween providing three circumferentially spaced perfusion pathways along an outer surface of the expanded balloon. The lobed shaped is formed for example by blow-molding the balloon parison in a mold having an inner chamber with the lobed shape. As is generally known for lobed balloons, a structure that prevents the balloon from taking a substantially cylindrical inflated shape is required, such as a reinforcing wall structure along the smaller outer diameter wall sections between each lobe. For example, bands that locally increase the balloon wall stiffness and constrain sections of the balloon from expanding during inflation can be used. Similarly, although not illustrated, the smaller outer diameter wall sections could be bonded to the underlying shaft section to form the lobes. Alternatively, separate, generally tubular balloon portions, each having an outer surface along the shaft, could be provided spaced around the circumference of the shaft, such that each separate balloon portion formed a lobe. To provide for perfusion, the lobed shape must extend at least along the proximal section of the working length of the balloon (proximal to the port 54) in the embodiment of FIG. 7. More generally, the lobed shape of the balloon extends along the entire maximum inflated diameter working length section of the balloon located between the proximal and distal inflatable tapered sections of the inflatable length of the balloon. However, in one embodiment, the lobed shape extends along the entire inflatable length of the balloon 50. In an alternative embodiment in which perfusion is not required, or is provided by a lumen other than the lobed perfusion path of lobed balloon 50, the balloon which extends circumferentially around the entire circumference of the shaft and which has eccentric section 52, inflates to a generally cylindrical (non-lobed) shape.

In the embodiment illustrated in FIG. 7, the catheter shaft 11 comprises an outer tubular member 55 having the inflation lumen 56 therein, and an inner tubular member 57 extending in at least a distal section of the outer tubular member and defining a wire lumen 58 therein configured to slidably receive the needle sheath tubular member 21. The outer and inner tubular members 55, 56 of the shaft are typically coaxially disposed such that the inflation lumen 56 is the coaxial space between the inner surface of the outer tubular member 55 and the outer surface of the inner tubular member 57. However, a variety of suitable catheter shaft designs can be used generally providing a wire lumen and an inflation lumen as are generally known. The balloon 50 has a proximal skirt section 59 sealingly secured around the circumference of the distal end of the outer tubular member 55, and at the opposite end has a distal skirt section sealingly secured around the circumference of the distal end of the inner tubular member 57, such that the inflatable interior of the balloon 50 is in fluid communication with the inflation lumen. The proximal skirt section, distal skirt section, and the section 53 are sealingly bonded to the underlying shaft (i.e., the outer and inner tubular members 55, 57) typically by heat fusion and/or adhesive bonding. The needle sheath tubular member 21, slidably disposed in the wire lumen 58 of the shaft inner tubular member 57, can be used as a guidewire for advancing the catheter within the patient's vasculature, and/or a separate guidewire (not shown) can be used for tracking the catheter to the desired location within the patient's vasculature and then exchanged for the needle sheath tubular member 21, as previously discussed. The balloon configuration of FIG. 7 could obviously alternatively be used with a fixed wire-type catheter shaft as discussed herein. In the over-the-wire catheter shaft design of FIG. 7, the shaft tubular member are operatively connected, typically at the proximal end, to allow for longitudinal movement of the needle sheath tubular member 21 but also ensure that the needle-through port(s) 14, 54 in the wall of the tubular member 21 and shaft inner tubular member 57 align so that the needle can be extended as desired out the port(s) 14, 54, and thereby avoid the needle puncturing the balloon inflation lumen which can otherwise occur if the shaft tubular members/needle are not correctly aligned with each other.

Figure 10:
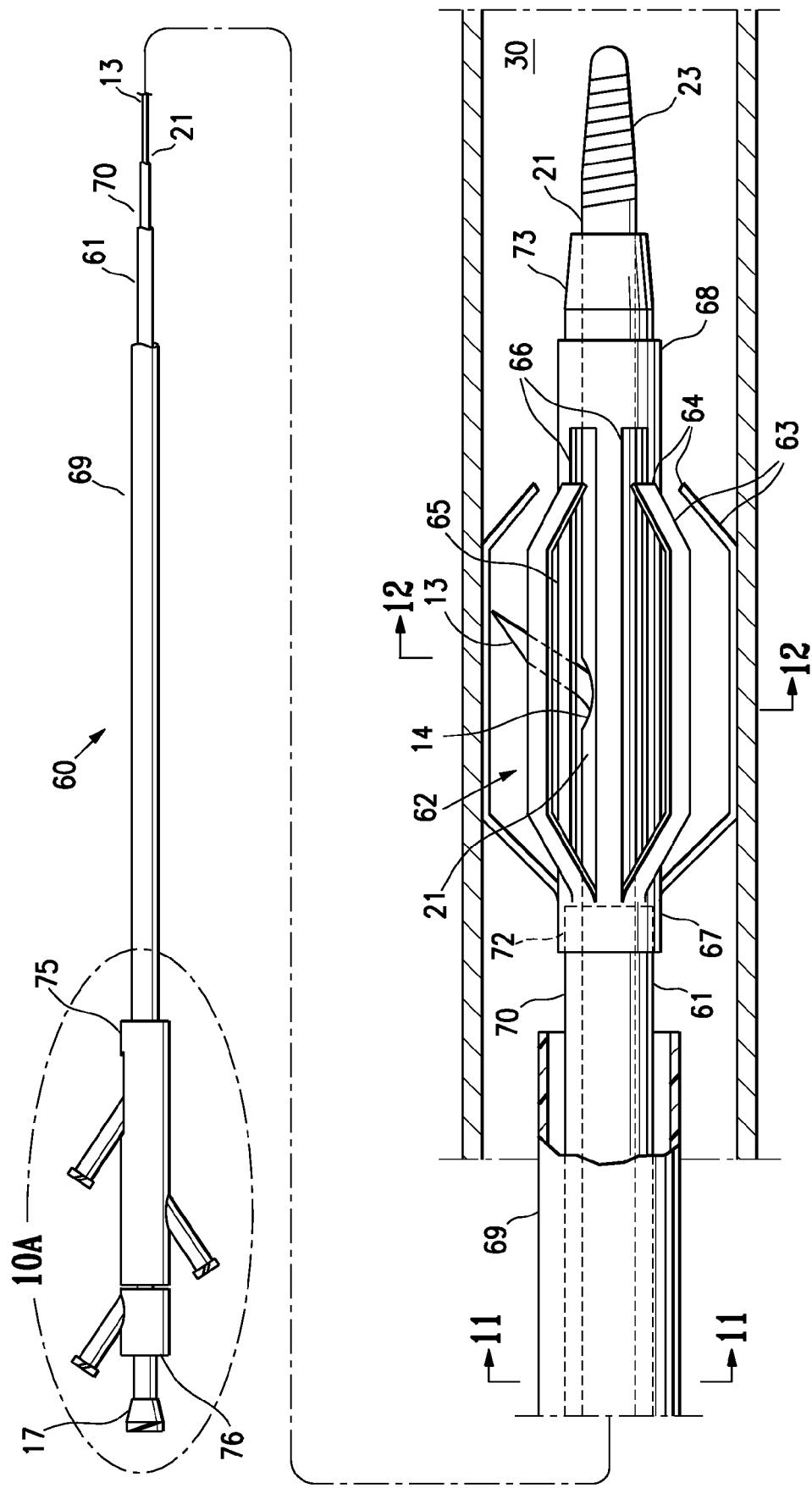
FIG. 10 illustrates an alternative embodiment in which the expandable member is a radially self-expanding open-walled frame having articulating struts with free distal ends, and a nonexpanding slotted section.

FIG. 10 illustrates an alternative catheter 60 embodying features of the invention, in which the expandable member is a radially self-expanding open-walled frame 62 on the catheter shaft 61, and the catheter includes an outer sheath 69 slidably disposed on the shaft 61, having an advanced configuration surrounding and slidably disposed on the frame 62 to constrain the frame in a collapsed configuration, and a retracted configuration which allows the frame 62 to radially self-expand. FIG. 10 illustrates the outer sheath 69 proximally retracted from the frame 62 so that the frame 62 is in the radially expanded configuration against the wall of the patient's body lumen 30. The catheter shaft construction can be otherwise similar to the embodiments discussed above, and similar elements are given the same reference numerals in the different embodiments. The catheter shaft 61 includes a needle sheath tubular member 21 defining the needle-through lumen 12 and port 14 configured to allow the needle 13 to be extended or retracted through the port 14 as discussed above. FIGS. 11 and 12 illustrate transverse cross sections of FIG. 10, taken along lines 11-11 and 12-12, respectively.

Similar to the embodiments in which the expandable member is an inflatable balloon, the frame 62 extends around the circumference and along an outer surface of the shaft 61 to substantially center the port 14 in the body lumen 30 in the expanded configuration, and has a portion which is at the radial location of the port 14 on the shaft side 28 opposite to the port-side 29 (see FIG. 12) of the shaft 61 and which expands into contact with the body lumen wall in the expanded configuration. Thus, the expandable frame 62 in the expanded configuration supports the shaft 61 in a position spaced away from the body lumen wall around the circumference of the shaft at the location of the port 14, and the needle 13 slidably exits the needle-through lumen 12 in the extended configuration through the port 14 spaced away from the body lumen wall as the expandable frame 62 supports the shaft at the port 14.

The expandable frame 62 generally comprises a plurality of struts. In the embodiment of FIG. 10 the frame 62 has longitudinally extending struts 63 which have a fixed first end, and a free opposite second end 64, and which are shaped to radially expand as the outer sheath 69 is retracted proximally along the frame 62 to thereby form the expanded configuration of frame 62, and the frame 62 further forms a non-expanding slotted tubular section 65 which has one or more longitudinally extending slots 66 in a side wall of the tubular section 65 configured to allow the needle 13 to laterally pass therethrough (a slot 66 thereby functioning in part as the catheter needle-through port). As best shown in FIG. 12, in the illustrated embodiment the frame 62 has a total of six struts 63 which expand into contact with the wall of the body lumen 30, two of which are completely located on the side 28 of the shaft opposite to the port-side 29 of the shaft. However, it should be understood that a variety of suitable frame designs can be used in accordance with the invention including a larger or smaller number of longitudinally extending struts. Although a frame having longitudinally extending struts is generally preferred for providing support at the needle-through port 14, the frame can alternatively or additionally have different strut designs including sinusoidal/circumferentially extending struts as are generally known for medical device expandable frames. The frame has an annular proximal skirt section 67 and an annular distal skirt section 68 configured for mounting the frame 62 on the shaft 61, although a variety of suitable configurations can be used to mount a radially expandable frame of the invention to the catheter shaft. The nonexpanding tubular section 65 extends from the proximal to the distal skirt section 67, 68 of the frame 62. In the illustrated embodiment, the free end 64 of the cantilevered struts 63 is the distal end of the struts, such that the fixed proximal end of the cantilevered struts 63 is fixedly secured to the proximal skirt section 67 of the frame 62. This configuration facilitates advancing and retracting the outer sheath 69 from the frame 62 to reversibly radially expand and collapse the frame 62, although the free end of the cantilevered struts 63 could alternatively be the proximal end of the cantilevered struts 63 if desired. The cantilevered struts 63 radially increase and decrease in profile (in response to the retraction or advancement of the outer sheath 69 thereover) without placing excessive stress on the catheter body, and allow for larger expanded diameters to be achieved from an initial tube size that has a minimal profile.

In the illustrated embodiment, the shaft 61 includes an inner tubular member 70 having a lumen 71 (see FIG. 11) configured to receive the needle sheath tubular member 21 therein. In the embodiment of FIG. 10, the frame proximal skirt section 67 is fixedly (i.e., non-moveably) secured to a distal end 72 (shown in dashed line in FIG. 10 under the proximal skirt section 67) of the inner tubular member 70, and the distal skirt section 68 of the frame 62 is mounted on a tubular distal tip member 73 having a distal port. In an alternative embodiment, the frame 62 may be integrally formed within the inner tubular member 70, as for example by laser cutting and forming spaced apart sections of the inner tubular member wall. The non-expanding slotted tubular section 65 (formed by the frame) provides a lumen extending distally from the distal end of the shaft inner tubular member 70, to thereby form a distal extension section of the shaft wire lumen 71. Thus, the needle sheath tubular member 21, slidably disposed in the wire lumen 71 of the shaft inner tubular member 70 and in the non-expanding slotted tubular section 65 and in the distal tip member 73, can be used as a guidewire for advancing the catheter within the patient's vasculature, and/or a separate guidewire (not shown) can be used for tracking the catheter 60 to the desired location within the patient's vasculature and then exchanged for the needle sheath tubular member 21, as previously discussed. Alternatively, the needle sheath tubular member 21 can be fixedly secured at the distal end of the frame 62 (e.g., to the frame distal skirt section 68 or to a distal tip member), such that the catheter is a fixed-wire type catheter.

The expandable frame 62 is typically formed of nickel-titanium (NiTi) alloy, such as shape memory material NITINOL, although a variety of suitable materials can be used including copper-zinc-aluminum, iron-manganese-silicon, and copper-aluminum-nickel shape memory materials, or non-shape memory materials such as stainless steel, cobalt-chromium, and the like. The expandable frame 62 of the embodiment of FIG. 10 can be fabricated from a tube cut or otherwise modified, for example using laser cutting, micromachining, chemical etching, electrical discharge machining, water jet cutting and the like, to form the slots 66 and the spaces which result in the cantilevered struts 63. Thus, the struts 63 and slotted section 65 are formed as an integral unit from a tube, although the frame 62 can alternatively be formed by a plurality of connected struts. When formed of a shape memory material, the cut wall of the tube is reshaped as part of a heat treatment process to form the cantilevered struts 63 in the radially expanded shape shown in FIG. 10. A non-shape memory material such as stainless steel is commonly deformed in a cold-working process (e.g., bending) to produce the desired shape. In one embodiment, the struts 63 are configured to fit into the slots 66 when the expandable frame 62 is collapsed by sheath 69. If the needle encounters a strut 63 during extension of the needle, the needle will often push the strut aside thereby creating an unobstructed path into the vessel wall. Alternatively, the struts are configured such that they are not in line with the needle extending out of the shaft. An embodiment with multiple needle-through ports 14 in tubular member 21 allows the needle to be advanced into multiple different injection sites in the body lumen wall without collapsing the struts and repositioning the catheter rotationally or longitudinally in the body lumen wall between subsequent injections.

Figure 10A:
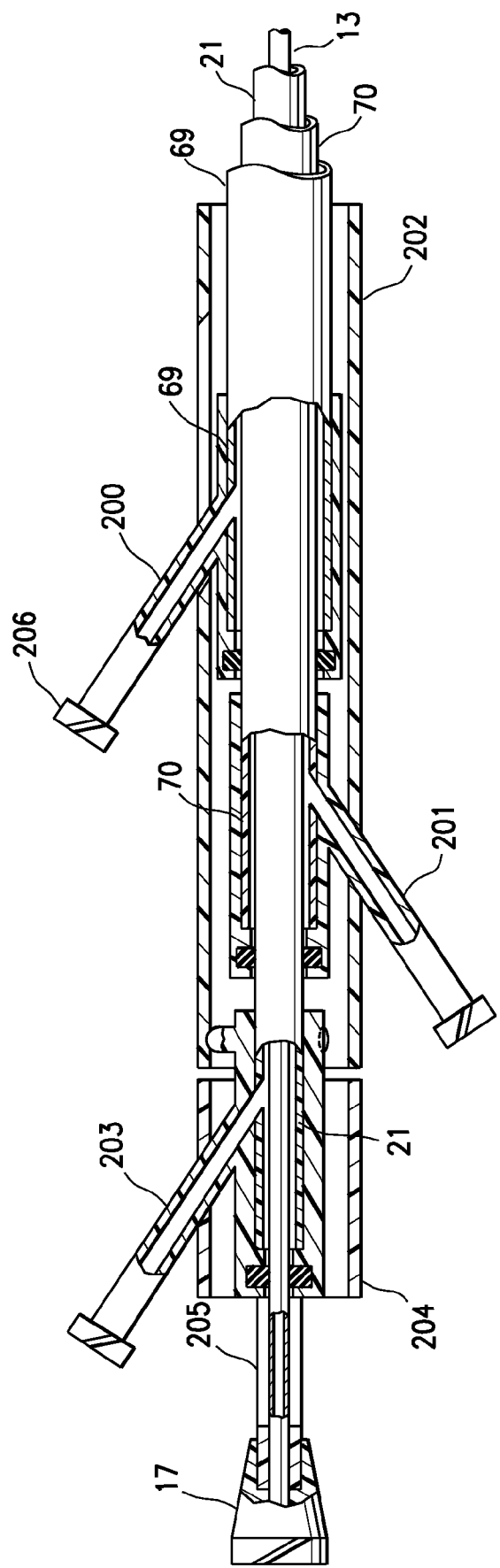

A proximal adapter assembly 75 is secured to the proximal end of the catheter shaft 61 and has a port 76 providing access to the needle sheath tubular member 21. Handle 17 is configured for placing the needle 13 in fluid communication with an agent source (not shown). Advancement and retraction of the needle 13 and outer sheath 69 is controlled at the proximal end of the catheter, allowing the catheter 60 to be deployed, the needle 13 extended, agent delivered to an injection site in the wall of the patient's body lumen 30, the needle 13 retracted, and the frame collapsed for removal or repositioning in the body lumen 30. The outer sheath 69 extends coaxially along the shaft proximal to the frame, and has a proximal end that can be manipulated by the physician to advance or retract the outer sheath 69, optionally using a proximal handle mechanism. The outer sheath 69, or a separate recovery catheter (not shown) can be advanced distally over the frame to radially collapse the frame, to allow the catheter to be repositioned or removed from the body lumen following delivery of agent to an injection site in the body lumen 30. To prevent the accidental contact of the needle tip with the struts 63 or other parts of the catheter, the proximal portion of the catheter typically configured to provide rotational orientation and longitudinal control of tubular member 21 relative to shat tubular member 70, such that the port 14/needle 13 path inside the struts is directed between the struts. FIG. 10A illustrates one embodiment of the proximal adapter assembly 75 useful with the over-the-wire catheter of FIG. 10.

In the embodiment of FIG. 10A, a hemostasis valve with sidearm 200 has its distal inner surface bonded to the outer surface of outer sheath 69 at the proximal end of outer sheath 69 Inner tubular member 70 continues proximally out of the proximal end of outer sheath 69 through the inner diameter (ID) of hemostasis valve with sidearm 200 and out of its proximal seal. In the absence of other constraints, this proximal seal allows the longitudinal and rotational motion of inner tubular member 70 within the seal. Hemostasis valve with sidearm 200 has a lumen that communicates with its ID (proximal of the proximal end of outer sheath 69) and its sidearm connection 206. Sidearm connection 206 may be a Luer connection suitable for connecting to a syringe or other medical fluid delivery apparatus. Fluid may be injected into sidearm connection 206 to flush the annular lumen between the ID of outer sheath 69 and inner tubular member 70. Fluid flow out of the proximal end of hemostasis valve with sidearm 200 is prevented or limited by the seal. Hemostasis valve with sidearm 201 is the same basic design as hemostasis valve with sidearm 200, except it is bonded to the proximal end of inner tubular member 70, and needle sheath tubular member 21 extends proximally out of its seal and fluid injected into its sidearm flushes the annular lumen between the ID of inner tubular member 70 and the outer diameter (OD) of needle sheath tubular member 21. Distal handle body 202 may be of a two or more piece design and encloses at least portions of hemostasis valves 200 and 201. Distal handle body 202 is designed such that hemostasis valve with sidearm 201 is completely constrained from any substantial motion relative to distal handle body 202. However, distal handle body 202 is also designed such that at least a portion of hemostasis valve with sidearm 200 is constrained within it in a manner, such that longitudinal motion of the hemostasis valve with sidearm 200 relative to distal handle body 202 is allowed, but only to proximal and distal limits. When hemostasis valve with sidearm 200 is moved to its proximal limit, outer sheath 69 is moved to a proximal position relative to inner tubular member 70 sufficient to allow the expansion of struts 63. When hemostasis valve with sidearm 200 is moved to its distal limit, outer sheath 69 is moved to a distal position relative to inner tubular member 70 sufficient to move over struts 63 and collapse them, as well as, if desired, to cover annular distal skirt section 68, such the annular gap between the ID of member 73 and the OD of tubular member 21 may be flushed by an injection at connection 206. Distal handle body 202 and hemostasis valves 200 and 201 thus are designed to mechanically interact/interfere in this manner when assembled. Distal handle body 202, the components 200 and 201 that it constrains, the components 69 and 70 and all the components attached to components 69 and 70 effectively comprise an independent catheter assembly. Needle sheath tubular member 21 extends proximally out of distal handle body 202 without being constrained by it. Hemostasis valve with sidearm 203 is also the same basic design as hemostasis valve with sidearm 200, except it is bonded to the proximal end of needle sheath tubular member 21, and needle 13 extends proximally out of its seal and fluid injected into its sidearm flushes the annular lumen between the ID of needle sheath tubular member 21 and the OD of needle 13. Connection 17 is attached to the proximal end of needle 13 and communicates with the ID of needle 13 such that fluid injected into connection 17 will travel through the lumen of needle 13 and out of its distal end. The proximal ends of shafts 205 are attached to either side of connection 17 in a longitudinally constrained manner. Proximal handle body 204 may be of a two or more piece design and encloses at least a portion of hemostasis valve with sidearm 203 in a manner that substantially prevents their relative motion. The distal ends of shafts 205 engage holes or slots (not shown) in the proximal handle body 204 such that connection 17 is constrained from rotation relative to the proximal handle body 204 and thus, the control of the rotational orientation of the needle 13 relative to port 14 is accomplished. The longitudinal motion of the distal ends of shafts 205 within proximal handle body 204 is constrained within proximal and distal limits and thus, the limits of the needle's extension out of port 14 and retraction into port 14 and the ID of needle sheath tubular member 21 are set, as desired. Proximal handle body 204 and the components that it directly or indirectly constrains effectively comprise an independent catheter assembly, which may be completely withdrawn proximally from the independent catheter assembly comprised of distal handle body 202 and the components that it directly or indirectly constrains. This allows a guidewire to be inserted in to the ID of inner tubular member 70 (and tubular distal tip member 73) during an over-the-wire insertion of the distal portion of the catheter assembly comprised of distal handle body 202 and the components that it directly or indirectly constrains. The guidewire may then be removed and the catheter assembly comprised of proximal handle body 204 and the components that it directly or indirectly constrains may be inserted into the proximal end of distal handle body 202, as shown. The distal end of proximal handle body 204 (or the distal end of hemostasis valve with sidearm 203) may be configured to engage the proximal end of distal handle body 202 in manner that conveniently releasably locks them together longitudinally and provides permits them to be rotated relative to each other at a desired rotational increment. For instance, an interference fitting protrusion and depression design, such that when the protrusion is fully engaged with the depression, the longitudinal position of the port 14 relative to the struts 63 is as desired (as shown) and is held in that position for the operator. Additionally, the shapes and orientations of the protrusion and depression may be chosen such that the rotational orientation of the port 14 relative to the struts is controlled such that the needle path is always between the struts and that the possible rotational increments of the port relative to the struts is controlled. For instance, a rectangular shaped protrusion and depression would allow engagement only at 180° rotational increments and an equilateral triangular shaped protrusion and depression would allow engagement only at 120° rotational increments. However, a variety of suitable handle designs can be used with a catheter of the invention. For instance, in some designs, the sheath 69 is so close fitting and the catheter materials and/or coatings are such that no connection 206 is necessary/no flushing of this annular lumen is required and thus, the sidearm of 200 may be omitted and/or replaced with something convenient for the operator to grasp when changing the position of 69 relative to 70. In another instance, the flushing and/or injection Luers may be configured to be at the ends of flexible tubes that are attached to the handle(s) or needle in a manner to be in communication with the desired lumen. In another instance, portions of 201 (and/or 203) may be incorporated into the design of portions of the handle body 202 (and/or 204). In another instance, flushing of the annular space between the ID of needle sheath tubular member 21 and the OD of needle 13 is not required, so the sidearm portion of 203 may be omitted.

FIG. 13 illustrates the distal section of an alternative embodiment of a catheter system having catheter 80 embodying features of the invention having a radially expandable frame 82 on the catheter shaft 81, with an outer sheath 69 having an advanced configuration (not shown) which collapses frame 82, and a refracted configuration which allows the frame to radially self-expand as illustrated in FIG. 13. The frame has struts 83 that extend longitudinally from the proximal to the distal skirt section 84, 85 of the frame 82, with a preformed radially expanded shape like the frame 62 of the embodiment of FIG. 10. However, unlike the embodiment of FIG. 10, both the proximal and distal ends of the struts 83 are fixed at the skirt sections of the frame. One of the skirt sections, typically the distal skirt section 85, of the frame 82 is slidably mounted over the shaft 81 to allow the struts to reversibly radially expand and collapse as the outer sheath 69 is slidably retracted or advanced thereover. The second skirt section (i.e., typically the proximal skirt section 84) of the frame is fixedly mounted to the shaft 81.

In the embodiment illustrated in FIG. 13, the shaft 81 comprises the needle sheath tubular member 21, which in the illustrated embodiment has a distal end section formed by a tubular member 86 secured to an inner surface of the distal end of a tubular member 87 forming the proximally adjacent section of the needle sheath tubular member 21. However, it should be understood that the needle sheath tubular member 21 can have a variety of suitable configurations including being formed of a single tubular member, or multiple tubular members joined end to end or in a layered structure. In the illustrated embodiment, the proximal skirt section 84 of the frame is mounted (e.g., fixedly) to the distal end of tubular member 87 of the needle sheath tubular member 21. In an alternative embodiment, the proximal skirt section 84 is fixedly secured to tubular member 86, and preferably abuts the end of tubular member 87, for a low profile. The distal end of tubular member 86, or a separate soft tip member secured thereto, forms the distal end of the tubular shaft 81. In one embodiment, the frame is mounted on the shaft such that the distal skirt section 85 does not slide distally a sufficient distance to slide over the more flexible distal tip. In an embodiment having a soft distal tip member secured to the distal end of tubular member 86, the distal end of the tubular member 86 is typically at the distal end of the distal skirt section 85 when the frame is in the collapsed configuration. The proximal end of the catheter 80 of FIG. 13 has a handle/connector, such as a connector similar to connector 17 to provide fluid communication with the lumen of the needle 13 as discussed above, and which typically allows the outer sheath 69 to incorporate into some portion of the handle.

The embodiment of FIG. 13 provides a very low profile device, with improved ease of manufacturing. Although shown for ease of illustration with a relatively large annular space between the outer sheath 69 and the shaft 81, it should be understood that the outer sheath 69 is typically sized to closely fit on shaft 81 to provide a low profile. In one embodiment, the distal tubular member 86 is formed of stainless steel or NITINOL (NiTi), and the proximal tubular member 87 has a proximal section formed of stainless steel, and a distal section formed of NITINOL. The expandable frame 82 and catheter shaft components (i.e., the needle sheath tubular member 21) may or may not be formed as integral parts from a single piece of material. In one embodiment in which the frame is integral with the shaft, the needle-through port 14 is at the proximal end of the frame and is longitudinally oriented, and the distal end of the frame is fixedly attached to the fixed wire tip. The fixed wire tip is configured to move distally when the frame is collapsing into the advancing outer sheath 69. The needle 13 would require a curve in its distal end to extend in a direction toward the vessel wall, and the needle 13 would therefore require rotational control (at the proximal handle) to avoid hitting a strut, but it could inject at desired angular intervals between the struts without rotating the entire catheter. The design facilitates using a relatively small needle.

A needle stop 88 in the wire lumen 12 of the needle sheath tubular member 21 is configured to contact the advancing needle 13, as for example by contacting a tapered section 89 of the needle 13, to set the extended length of the needle 13 as it extends through the port 14. The needle stop 88 ensures that the needle will repeatedly advance to the same maximum injection depth when distally advanced by the operator, and a variety of suitable needle stop configurations can be used with a catheter of the invention as discussed in more detail below. The needle stop 88 can be used to join two adjacent sections of the needle sheath tubular member 21 together (such as the proximal and distal sections of the proximal tubular member 87) by press fitting or otherwise bonding the needle stop within both sections to thereby span the junction. Because the needle 13 is relatively long, floppy and sharp, it should be constrained/kept inside of shaft 81 (typically by a proximal handle) to avoid a loss of sterility, sharpness, sharp tip engagement with 88, kinking during insertion into 81 and to avoid puncturing personnel and equipment.

Similar to the embodiments of FIGS. 1 and 6, the lumen 12 of the needle sheath tubular member 21 has a closed distal end, with ramp 24 in the needle sheath tubular member 21 at the proximal end of the port 14, and the ramp 24 is typically provided by a distal tip member having a distal end secured to the flexible distal tip coil 23 of the catheter, such that the catheter 80 is a fixed wire catheter.

In a method of using a catheter of the invention, such as catheter system of FIG. 13 having catheter 80, to delivery an agent to a patient's targeted anatomy, a guidewire is advanced through the patient's vasculature to a targeted site in the body lumen 30, such as a coronary blood vessel (and preferably initially to the most distal targeted site in the vessel if there is more than one targeted site in the vessel). The outer sheath 69 is delivered over the guidewire until its distal end is distal to the targeted site. The guidewire is then removed, leaving the outer sheath 69 in place. The catheter 80 is then inserted into the proximal end of the outer sheath 69, which constrains the frame 82 in the low profile, collapsed configuration, allowing the catheter to be tracked through the outer sheath until the frame is adjacent to the target site. Therefore, in one embodiment of the catheter 80 of FIG. 13, the shaft 81 and outer sheath 69 are not permanently coaxially disposed together, and thus the shaft 81 is configured to be completely removed from outer sheath 69 prior to introduction of outer sheath 69 into the patient's body lumen 30. Location of the frame can be verified under fluoroscopy, and optional radiopaque marker bands or other marking features on the catheter visualized to facilitate catheter positioning in the body lumen 30. Additionally or alternatively, the outer sheath 69 has radiopaque markers that are positioned at the targeted site before or after the catheter is inserted, and the lengths and engagements of the catheter shaft 81 and outer sheath 69 at the proximal handle of outer sheath 69 are such that the frame 82 is properly positioned at the desired target site relative to the outer sheath markers when the outer sheath 69 is in its distal advanced configuration. The outer sheath 69 is then proximally retracted until its distal end is proximal to the frame 82, so that the frame 82 will recover to its expanded configuration, thereby contacting the wall of the body lumen 30 to provide centering and support to the catheter 80. The needle 13 is then advanced through the port 14 in the needle sheath tubular member 21 and through the struts 83 of the frame 82 until it penetrates the target tissue of the wall of the body lumen 30, and agent is caused to flow through the needle lumen and out the distal tip of the needle from an agent source connected to the proximal end of the catheter. After the flow of agent is stopped, the needle is proximally retracted into the lumen 12 of the needle sheath tubular member 21, and the outer sheath 69 is distally advanced over at least a proximal section of the frame 82 to collapse and constrain the frame 82 in the low profile configuration. Following optional additional injections, the outer sheath 69 and catheter 80 may then be removed from the patient to complete the procedure. Additional injections may involve the rotation and/or proximal repositioning of outer sheath 69 and catheter 80 before outer sheath 69 is withdrawn. If an additional injection requires the distal advancement of outer sheath 69 and catheter 80, the catheter 80 may be withdrawn from outer sheath 69, the guidewire replaced, outer sheath 69 advanced to the new distal position, and the procedure for injection repeated as discussed above. In some instances, catheter 80 is left in outer sheath 69 and its fixed wire distal tip used to select a path moving distally into the anatomy by rotating the entire assembly of outer sheath 69 on catheter 80. In another method, the catheter 80 is advanced together with the outer sheath to the desired treatment site, and if difficulty negotiating the tortuous anatomy is encountered, the catheter 80 may be proximally withdrawn and replaced with a guidewire, and the after positioning, the guidewire is exchanged for the catheter 80 and the deployment and injection procedure proceeds as outlined above.

In embodiments in which the catheter of the invention includes a wire lumen configured to slidably receive a guidewire or the needle sheath tubular member 21, the catheter may be advanced together with the outer sheath 69 or within a previously introduced outer sheath 69 (i.e., within an outer sheath that was previously distally advanced to the treatment site as discussed above) together with the guidewire or over a previously introduced guidewire to the desired treatment site. The guidewire is then exchanged for the needle sheath tubular member 21 and the deployment and injection procedure proceeds as outlined above.

The needle sheath tubular member 21 floppy tip coil 23 is preferably configured to provide for some directional control by the distal end of the catheter, such that the needle sheath tubular member 21 can be used to select a desired distal branch of the patient's anatomy without having the reintroduce a guidewire in order to direct the catheter into the desired distal branch. The fixed wire tip is bent during manufacturing or is designed to be bent by the physician as desired. Similar positioning, deployment, and injection procedures are used in embodiments of the invention in which the expandable member is an inflatable balloon, although the expandable member is deployed by inflating the balloon with an inflation fluid rather than proximally retracting an outer sheath 69. Embodiments having an inflatable balloon as the expandable member can be positioned at the target site by being slidably advanced within a previously introduced support catheter similar to the outer sheath 69 as discussed above for fixed-wire catheter 80.

FIG. 14 illustrates an embodiment of a catheter 90 having the frame 82 mounted on a shaft that further comprises an inner tubular member 91 with a wire lumen 92 having the needle sheath tubular member 21 slidably disposed therein. Thus, the frame 82 is mounted on the inner tubular member in the manner discussed above in relation to the embodiment of FIG. 13, with a fixed first end (e.g., the proximal end of the frame) and a slidably mounted second end (e.g., the distal end of the frame), to allow the frame to radially expand and collapse as the outer sheath 69 is withdrawn or advanced. The inner tubular member 91 has an atraumatic distal tip as previously discussed, which in embodiment of FIG. 14 is a soft distal tip member 93 secured at the distal end of the inner tubular member 91 to facilitate atraumatically advancing the catheter in the patient's body lumen 30. The junction between tip member 93 and inner tubular member 91 is shown in dashed lines under the distal skirt section 85 of the frame 82 in FIG. 14.

In the embodiment illustrated in FIG. 14, the inner tubular member has a plurality of ports 95 in a sidewall section surrounded by the radially expanding maximum diameter section of the frame 82. The multiple ports 95 may be randomly positioned or arranged in a pattern, to permit the injection needle 13 to pass from the inside to the outside of the catheter shaft at a variety of locations. As best shown in FIG. 15 illustrating a transverse cross section of FIG. 14, taken along line 15-15, the needle-through port 14 of the needle sheath tubular member 21 must be rotationally and longitudinally aligned with one of the ports 95 of the inner tubular member to allow the needle 13 to exit the distal section of the shaft inner tubular member 91. The catheter is configured for properly aligning the needle-through lumen 14 with one of the ports 95, while still allowing the needle sheath tubular member 21 sufficient freedom of movement within the inner tubular member 91 to allow for any of the ports 95 to be the selected port. The distribution of ports 95 along the expandable section of a single frame 82 can take a variety of forms, in which the multiple ports 95 are circumferentially and/or longitudinally spaced apart to facilitate delivery of agent to a desired injection site. Additionally, multiple ports 95 spaced apart around the circumference at a single radial location, or along a relatively short longitudinal length, ensures that injections may be made in several angular locations at a diseased length of the vessel. For example, in one embodiment, the shaft has two injection ports 95, spaced 180 degrees from each other within the expandable length of a single frame 82. The expandable length of a single expandable frame in one embodiment is about 10 mm.

FIG. 16 illustrates a distal section of an alternative embodiment of the inner tubular member 91 in which the multiple sidewall ports 95 are replaced by a spiral gap 97 defined by a helically extending open-walled section. The helically extending wall 96 is formed by cutting the spiral gap 97 through the wall of the inner tubular member 91, or by other coiled structures. The spiral gap 97 formed by the helical turns 96 of the wall of the inner tubular member 91 provide passages for the injection needle, while defining an extension of the wire lumen 92 of the inner tubular member 91 configured to slidably receive the needle sheath tubular member 21 therein. For ease of illustration, the needle sheath tubular member 21 and the expandable frame 82 are not illustrated in FIG. 16, but the frame 82 would be mounted on the inner tubular member 91 as discussed above with the frame proximal and distal skirt sections 84, 85 at either end of the open-walled section.

Figure 17:
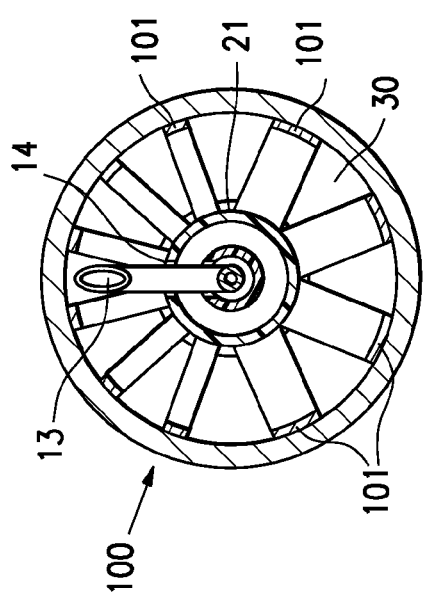
FIG. 17 illustrates an alternative embodiment in which the struts of the frame are thicker on the shaft side opposite to the port-side of the shaft.

One aspect of the invention is directed an expandable frame 100 configured to provide a level of support to the catheter shaft that varies around the circumference thereof, by having a varying width or thickness dimension or density around the circumference of the frame. For example, FIG. 17 illustrates a transverse cross section taken at the location of port 14 (which provides for lateral egress of the needle 13 from the shaft 21) of an embodiment in which the frame struts 101 have a varying width around the circumference of the frame 100. More specifically, the struts 101 which are radially expanded on the side of the shaft opposite to the port-side of the shaft have a greater width than the struts on the port-side of the shaft. The struts 101 have the larger and smaller widths illustrated in FIG. 17 along the entire length of the struts or alternatively along just a portion of the length of the struts extending along the port 14 of the shaft. The frame 100 may be as otherwise described above in relation to the previous embodiments, such as frames 62, 82 of FIGS. 10 and 14, respectively. Although not illustrated in FIG. 17, it should be understood that the catheter shaft may include an inner tubular member, such as inner tubular member 91, on the needle sheath tubular member 21, as previously discussed.

In the embodiment illustrated in FIG. 17, the entire side of the shaft opposite to the port-side has the wider struts 101 in the expanded configuration, for maximizing the extra support provided by the frame 100 opposite to the needle-through port 14 of the shaft 21. However, the wider struts 101 could be more sparsely distributed, such that, more generally, one or more wider struts 101 are at least provided at the position on the wall of the patient's body lumen 30 located furthest from the needle 13 penetration site. Preferably, none of the wider struts are provided on the port-side of the shaft in the expanded configuration. In the illustrated embodiment, the width of the narrower struts 101 on the port-side of the shaft is about 50% of the width of the wider struts 101 on the opposite side of the shaft. However, the difference in size can vary, depending on the level of support that is desired. The width of the struts 101 and the number of wider as opposed to narrower struts is selected to provide the desired level of the support to the shaft, and typically also to, as much as possible, provide a frame that collapses toward a complete circular shape prior to and after radial expansion, for even distribution of torque and bending in the collapsed state as discussed in more detail below regarding the embodiment of FIGS. 18A and 18B. A frame having struts such as the variable width struts 101 of FIG. 17 will radially collapse to a shape that is not a complete circle (e.g., somewhat oval or with uneven distance between the struts).

Figure 18B:
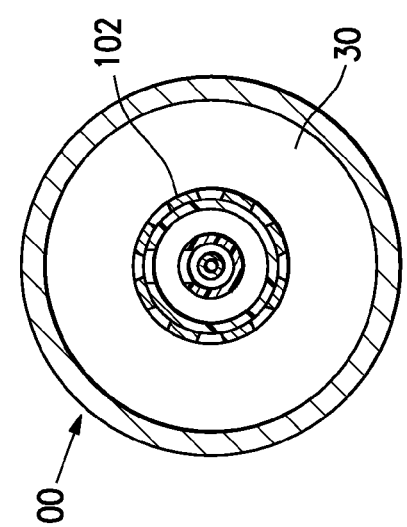
FIG. 18B illustrates the frame of FIG. 18A in the collapsed configuration.
Figure 18A:
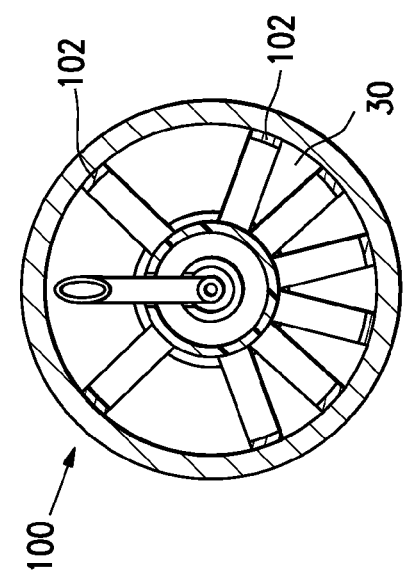
FIG. 18A illustrates an alternative embodiment in which the struts of the frame are more densely spaced together on the shaft side opposite to the port-side of the shaft in the expanded configuration.

FIGS. 18A and 18B illustrate a transverse cross section of an alternative embodiment of the frame 100, in which the frame has substantially uniform width struts 102, at least at the radial location of the port 14, of a varying density (i.e., number) around the circumference of the frame 100. More specifically, the frame has a greater density of struts 102 which radially expand on the side of the shaft opposite to the port-side of the shaft than on the port-side of the shaft. In the illustrated embodiment, the port-side of the shaft has one third the number of struts on the opposite side of the shaft. However, the difference in density can vary, depending on the level of support that is desired, such that the port-side of the shaft generally has at least one less strut than the opposite side of the shaft. In the illustrated embodiment, because the struts 102 have substantially uniform widths (i.e., uniform within normal manufacturing tolerances), the frame will radially collapse to form a complete circle, as shown in FIG. 18B illustrating the frame of 18A in the radially collapsed configuration. Although illustrated with some slight space between the adjacent collapsed struts 102 in FIG. 18B for ease of illustration, it should be understood that the struts 102 can collapse to a complete circle with the struts 102 touching. It is preferred to make each strut the same width, to thereby distribute bending and torque stresses evenly throughout the collapsed structure, in order to maintain optimum torque transmission and flexibility in the collapsed state for improved catheter deliverability.

In the embodiment of FIGS. 18A,B, as the frame radially expands, the struts tend to bow outwardly and downwardly, causing them to be on the side of the shaft opposite to the port-side in the expanded configuration. The struts thus have a directional bias in the expansion path, rather than following a uniform radial path from the collapsed to the expanded configuration. This bias toward one side of the shaft/body lumen wall by some of the struts 102 can be provided by preshaping the struts 102 during the manufacturing process. For example, struts 102 formed of a shape memory material can be formed in the desired shape in a fixture and heat treated to impart the desired shape memory shape. Suitable shape memory materials for the frame struts 102 include metals such as NiTi alloy, biodegradable polymers such as oligo(e-caprolactone)diol, and nonbiodegradable polymers such as polynorborene.

Figure 19:
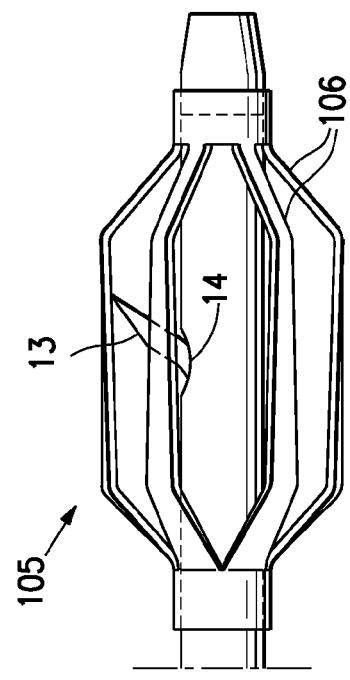
FIG. 19 illustrates an alternative embodiment in which the thickness of the struts of the frame decreases distally.

In an alternative embodiment of a catheter frame providing variable support, the width or the thickness of the struts varies along the length of the struts. For example, in the embodiment of FIG. 19, the frame 105 has struts 106 with a width that decreases distally along the length of the struts. As a result, more support is provided by the frame toward the proximal end of the expandable section of the frame. When the needle 13 is advanced laterally from the shaft (e.g., needle sheath tubular member 21), it typically travels a path having a distally advancing component, such that the reactive load will be directed along the needle to the shaft toward the proximal end of the frame 105. Because the frame is more robust along the proximal section, it provides improved support to the shaft as the needle contacts and penetrates the tissue. Additionally, the distally increasing flexibility of the frame facilitates advancing the catheter through the patient's anatomy during catheter delivery. Although illustrated with a varying width in FIG. 19, it should be understood that the frame struts could alternatively have a varying thickness therealong. Because the primary loading condition of the struts is bending in this case (i.e., the struts react to the load of the reaction force of the needle by bending to maintain the shaft position, it would be expected that a more significant variation in structural stiffness will be realized by varying the strut thickness as opposed to the strut width. Varying the thickness of the struts could be accomplished by, for example, an etching process. However, varying the width of the struts, for example by laser cutting, has manufacturability advantages when compared with having to vary the thickness of the struts.

Figure 20:
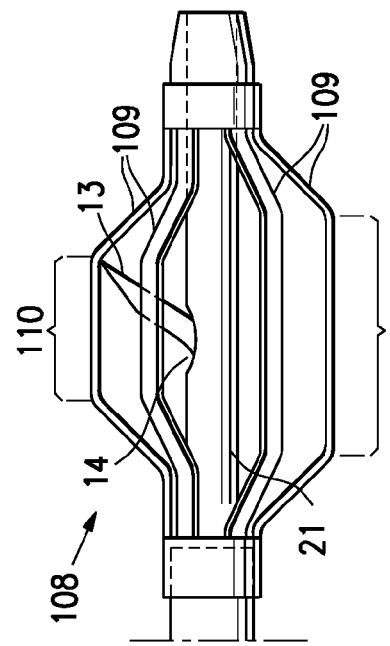
FIG. 20 illustrates an alternative embodiment in which the struts of the frame have a shorter working length on the port-side of the shaft.

FIG. 20 illustrates an alternative embodiment of a catheter frame 108 providing variable support, in which the variation in radial stiffness is achieved by varying the working length of the struts 109 of the frame, such that circumferentially spaced struts have a longer or a shorter working length depending on the location relative to the needle-through port 14 of the shaft. The terminology "working length" refers to the part of the expandable section of the frame that is configured to radially expand into contact with the surrounding wall of the patient's body lumen. In the embodiment of FIG. 20, the frame struts on the port-side of the shaft have a working length 110 that is shorter than the working length 111 of the struts on the opposite side of the shaft (e.g., needle sheath tubular member 21). The longer working length 111 is expected to provide greater support in the expanded configuration in the patient's body lumen and is therefore advantageously provided opposite to the injection site on the side of the shaft opposite to the port-side of the shaft. Additionally, in curved sections of the patient's body lumen 30, the longer working length 111 provides greater support over longer curves.

The variable support frames are thus configured to provide improved catheter support, which preferably reduces the risk of locating the needle in the wrong place during penetration, to thereby facilitate accurate placement of the agent at a desired injection site. The risk of vessel perforation is also preferably reduced, as the physician is less likely to overcompensate in the needle's advancement in order to penetrate the vessel wall.

Figure 21:
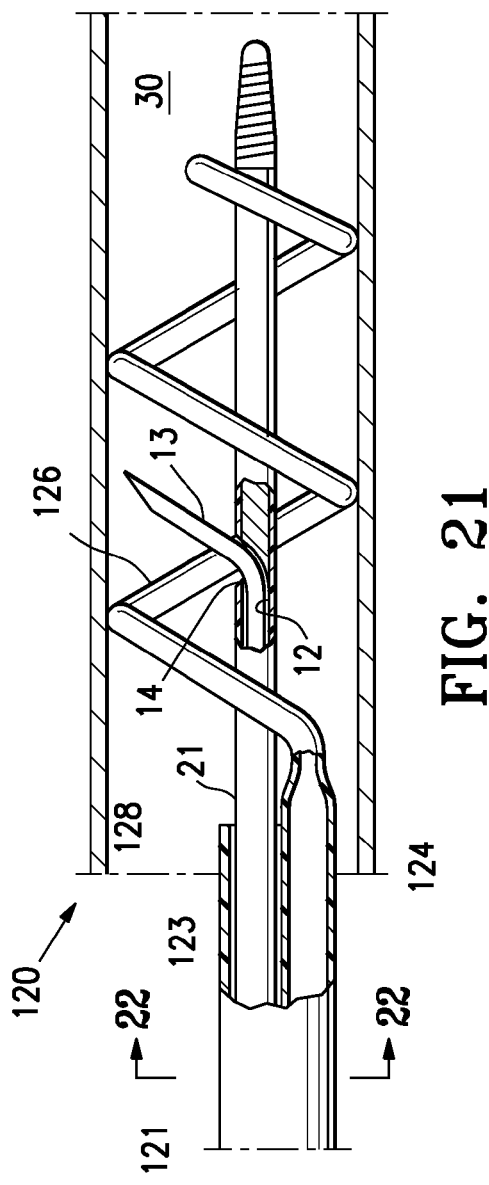
FIG. 21 illustrates an alternative embodiment in which the shaft includes an outer tubular member, and the expandable member is a distal section of the shaft outer tubular member which is biased to radially expand to a preshaped spiraled or zigzagged configuration upon removal of the straightening element or fluid from a second lumen in the distal section of the shaft outer tubular member.
Figure 22:
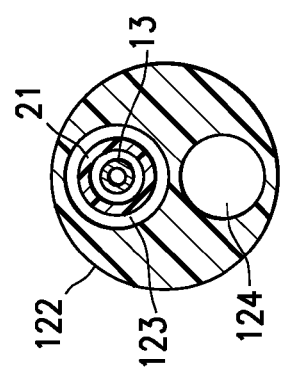
FIG. 22 is a transverse cross section of FIG. 21, taken along line 22-22.

FIG. 21 illustrates an alternative catheter 120 embodying features of the invention, in which the expandable member is a distal section of the shaft which is biased to radially expand to a preshaped spiraled or zigzagged configuration upon removal of a straightening element or fluid from an lumen of the shaft. Specifically, in the embodiment of FIG. 21, the shaft 121 includes a needle sheath tubular member 21 defining the needle-through lumen 12 and port 14, and an outer tubular member 122 having a first lumen 123 having the needle sheath tubular member 21 slidably disposed therein, and having a second lumen 124 which is eccentric to the first lumen 123 and which extends distally of a distal end of the first lumen and which is configured to receive a straightening element 125 (see FIG. 23) or fluid therein, and the expandable member is a preshaped helical distal portion 126 of the shaft outer tubular member 122. FIG. 21 illustrates the catheter 120 with the preshaped distal portion in its radially expanded spiraled relaxed configuration (i.e., after removal of the straightening element from the second lumen 124 in the distal section of the shaft outer tubular member 122). FIG. 22 illustrates a transverse cross sectional view of the catheter of FIG. 21, taken along line 22-22. In the relaxed, radially expanded configuration, the preshaped distal portion 126 of the outer tubular member 122 is configured to contact the wall of the body lumen such that it centers and stabilizes the distal shaft section within the patient's body lumen 30.

Figure 23:
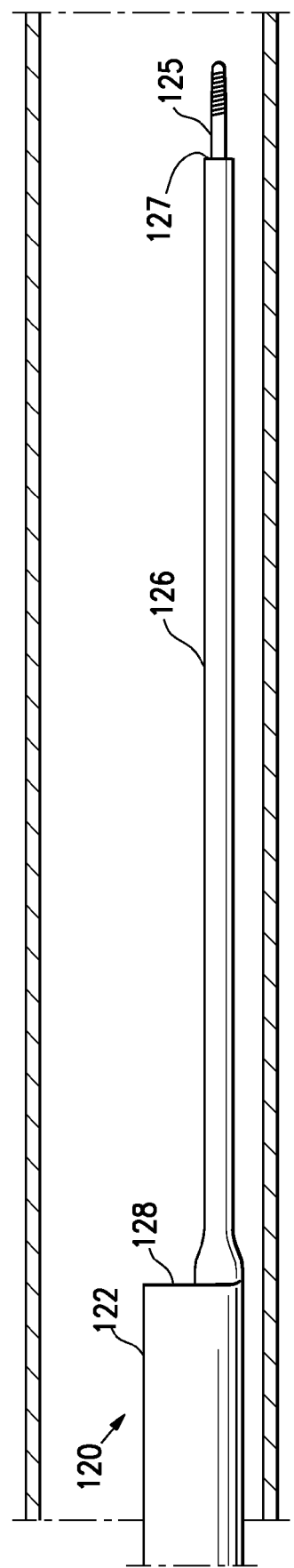
FIG. 23 illustrates the catheter of FIG. 21 with the shaft outer tubular member in the straightened configuration with a guidewire slidably disposed therein.

FIG. 23 illustrates the catheter 120 of FIG. 21, with the preshaped distal portion 126 in a straightened configuration resulting from the straightening element 125 being disposed in lumen 124, and with the needle sheath tubular member 21 proximally withdrawn into the shaft first lumen 123. The straightening element 125 is typically a guidewire having a flexible distal tip coil, or a stylet. In the illustrated embodiment, the second lumen 124 has a port 127 at the distal end thereof, and is configured for slidably receiving a guidewire-type straightening element 125 therein. In an alternative embodiment, the second lumen 124 is a blind (closed end) lumen, such that a fluid filling the second lumen 124 can act as the straightening element. The second lumen 124 thus extends from the proximal to the distal end of the catheter 120, and is in communication with a proximal adapter (not shown) on the proximal end of the catheter shaft 121. The proximal adapter has a first port which provides access to the first lumen 123, and a second port which provides access to the second lumen 124 of the catheter shaft. The catheter 120 can be advanced within the patient's vasculature over the guidewire-type straightening element 125 in the low profile configuration illustrated in FIG. 23. During delivery, at least a distal section of the first lumen 123 may be unloaded (i.e., the needle sheath tubular member 21 proximally withdrawn therefrom), to provide maximum flexibility to facilitate slidably advancing the catheter 120 within the patient's vasculature. Once at the target location in the body lumen 30, the guidewire-type straightening element 125 is proximally retracted to allow the preshaped distal portion 126 to assume its radially expanded configuration. The straightening element 125 can be partially or fully withdrawn from the lumen 124. The shaft needle sheath tubular member 21 is then advanced in the first lumen 123 out the port 128 of the shaft outer tubular member 122 to an advanced position as illustrated in FIG. 21, until the needle-through port 14 is in a desired position to allow the needle 13 to be extended laterally from the shaft (e.g., needle sheath tubular member 21) between turns of the spiraled (or zigzagged) distal portion 126. In an alternative embodiment, the needle sheath tubular member 21 is fixedly secured to the outer tubular member 122 in the advanced position. Although not illustrated, a zigzagged distal port 126 typically extends from side to side of the shaft similar to the spiraled distal portion 126 but with more abrupt, shaper turns. The preshaped distal portion 126 of the shaft outer tubular member 122 can be formed using a variety of suitable methods, such as cold working, or heating and then cooling the extruded distal portion within a mold having the desired spiral or zigzag shape, or using a secondary spiraled/zigzagged element in the lumen 124 to impart the biased radially expanded shape.

In the embodiment in which the second lumen 124 is configured to slidably receive a guidewire 125, the second lumen is slightly larger than the guidewire, and is preferably smaller than the first lumen 123 which is configured to slidably receive the needle sheath tubular member 21 (e.g., the second lumen 124 is about 0.016 inches in diameter for a 0.014 inch diameter guidewire, and the first lumen 123 is about 0.020 inches in diameter). In an alternative embodiment in which the second lumen 124 is configured to be straightened by filling with a fluid, the fluid (e.g., saline, contrast, water) is introduced into the fluid-tight second lumen 124 until the pressure increases sufficiently to straighten the preshaped distal portion 126. In this embodiment, the walls of the preshaped distal portion 126 are relatively thin, and the spiral or zigzag turns are substantially stacked (in contact or nearly in contact) in the relaxed radially expanded shape, to allow the force of the introduced fluid to be directed toward straightening the preshaped distal portion in the most effective manner. The substantially stacked turns would be closer together than in the embodiment illustrated in FIG. 21, but would have at least a pair of turns with a space in between to allow for the needle 13 to be extended through the expanded distal portion 126 into the wall of the patient's body lumen 30.

In one embodiment, a catheter of the invention has multiple expandable members longitudinally spaced along the shaft. For example, multiple expandable frames, such as frame 82, placed in tandem provide multiple locations for advancement of the injection needle 13. Specifically, in one embodiment, a catheter of the invention has a one or more additional expandable frames longitudinally spaced from the first frame on the distal shaft section, so that the needle sheath tubular member 21 is configured to be slidably advanced to one or more of the frames for positioning the needle 13 at different injection sites in the patient's body lumen 30. The tandem frames are preferably used in embodiments having the needle sheath tubular member 21 slidably disposed in an inner tubular member of the shaft, as discussed above in the embodiments of FIGS. 10 and 14, to facilitate moving the needle 13 between the longitudinally spaced apart frames. A suitable spacing between the frames (i.e., between the distal end of a proximal frame and the proximal end of the distally adjacent frame) is about 30 mm in one embodiment, although a variety of suitable spacings can be used. Each tandem frame would surround one or more needle-through ports 14 in the wall of the shaft which allow the needle 13 to exit the shaft. In one embodiment, the longitudinally spaced apart tandem ports 14 in the wall of the shaft, surrounded by the expandable section of each frame, are circumferentially spaced apart (i.e., radially misaligned) in a clocked array around the circumference of the shaft. By thus "clocking" the arrangement of the tandem ports, the distribution of agent throughout the body lumen wall is improved, by facilitating delivery of agent to multiple injection sites spaced around the circumference of the body lumen wall as opposed to only one angular segment of the body lumen wall.

An injection may be made at each location where an expandable tandem frame is deployed, and preferably the catheter is configured so that the injected agent will spread through the vessel wall between the expandable frames. This ensures that the desired length of vessel is treated, without untreated gaps existing longitudinally between the injection sites, and without the need to collapse and redeploy the frames in alternative longitudinal locations. The tandem expandable members thus improve the ease of delivery, in that the physician will not need to reposition and redeploy the catheter after the first injection. Rather, after one or more injections at the location of the first of the tandem frames, a second injection can be made at the location of the second tandem frame by merely advancing or retracting the needle sheath tubular member 21 relative to the deployed tandem expandable members, without moving the entire catheter. As a result, the overall procedural duration is potentially reduced for enhanced procedural safety.

FIGS. 24-27 illustrate alternative embodiments of the expandable member frame, in which the frame has at least a portion configured to elongate or compress as the distal shaft section and frame thereon bend in a curved section of the patient's body lumen. Specifically, the frame is configured to adjust to the vessel anatomy when deployed along a bend in a vessel, or as the vessel pulsates causing a change in vessel geometry. In the embodiment illustrated in FIG. 24, the expandable member frame 130 is formed of struts extending longitudinally between a first (e.g., proximal) end of the frame fixedly secured to the shaft and a second (e.g., distal) end of the frame slidably mounted on the shaft, and each longitudinally extending strut has a curvilinear portion 131 with undulations between the first and second ends of the frame configured to elongated or compress as the catheter distal section and frame 130 thereon bend in a curve. In the illustrated embodiment, frame 130 is mounted on the needle sheath tubular member 21 of the catheter shaft. The curvilinear portion 131 is located between the expandable tapered sections of the frame, along a working length section of the frame configured to radially expand into contact with the wall of the patient's body lumen 30. The curvilinear portion 131 has a proximal end proximal to the needle-through port 14 and a distal end distal to the needle-through port 14, although a variety of suitable length curvilinear portions 131 can be used. The curvilinear portion 131 typically extends longitudinally along all or a majority of the working length section of the frame, and compresses/elongates in response to axial loads more readily than in response to radial loads, such that adequate centering and support for the catheter shaft is provided by the frame 130. As shown in FIG. 25, illustrating the frame 130 and distal shaft section bending in a curved section of the patient's body lumen 30, the struts independently elongate or compress to accommodate the necessary length changes, such that the struts near the inner radius of the curved section of the body lumen 30 will compress in length, and the struts closer to the outer radius of the curve will correspondingly elongate. Consequently, the frame 130 adjusts to the anatomy, thereby minimizing trauma and stress on the body lumen wall.

In the embodiment of FIGS. 24 and 25, the undulations 132 are oriented radially inwardly. FIG. 26 illustrates an elevational view of an alternative embodiment in which the curvilinear portion 131 has undulations 133 which turn in a plane substantially parallel to the longitudinal axis of the frame, such that the undulations 133 are not oriented radially inwardly or radially outwardly. As a result, the curvilinear portion does not decrease the available perfusion path area inside the frame, and structural interference with blood flow is limited. A variety of suitable undulations can be used in curvilinear portions, configured to compress or lengthen in a spring-like manner, although the sinusoidal type undulations such as in the embodiment of FIG. 26 are typically preferred for facilitating a desired range of elongation and compression without disadvantageously effecting frame characteristics.

FIG. 27 illustrates an elevational view of an alternative embodiment in which the expandable member frame 135 is formed of helically extending struts spiraling around the shaft from a first (e.g., proximal) end fixedly secured to the shaft to a second (e.g., distal) end slidably mounted on the shaft. The helically extending struts extend from proximal to distal of the needle-through port 14, to thereby elongated at the outer radius of a curved section of the body lumen or compress at the inner radius of the curve, as the catheter distal section and frame thereon bend in the curve. Similar to the embodiment of FIG. 24, the frame 135 is illustrated mounted on the needle sheath tubular member 21 of the shaft, although a variety of shaft designs can be used. Additionally, the frame 135 is capable of adjusting to torsional loads (i.e., winding or unwinding), which is specifically advantageous in anatomies with significant torsional strain during pulsation, such as the SFA (superficial femoral artery).

FIG. 28 illustrates an elevational view of an alternative embodiment configured to adjust to the vessel anatomy when deployed along a bend in a vessel, or as the vessel pulsates causing a change in vessel geometry, in which the expandable member frame 140 has a proximal end 141 fixedly secured to the shaft proximal to the needle-through port 14, and a free distal end 142 which is located distal to the needle-through port and which radially expands against the wall of the patient's body lumen 30 in the expanded configuration, and is axially spaced from a second frame 145 having a proximal end 146 fixedly secured to the shaft and a free distal end 147. In the illustrated embodiment, the second frame 145 is distally spaced on the shaft from the expandable member frame 140, although it could alternatively be proximally spaced from the frame 140, such that it does not surround a needle-through port of the shaft. Thus, the second frame 145 is not supporting the shaft at the location of a needle-through port such as port 14. Because the struts of the frame 140 are independent from the struts of the second frame 145, the pulsation of the wall of the body lumen and the resulting changes in vessel geometry translate to each frame 140, 145 independently. Therefore, the frames 140, 145 respond independently of each other, which improves the overall flexibility of the catheter and conformability to the vessel.

Figure 29:
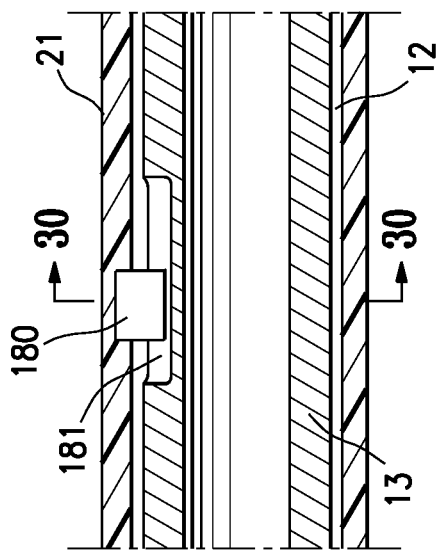
FIG. 29 illustrates a catheter embodying features of the invention having a shaft and a needle slidably disposed in a lumen of the shaft and having a rotational alignment feature, formed by mating surfaces of the shaft and needle, in which the outer surface of the needle has a groove.
Figure 30:
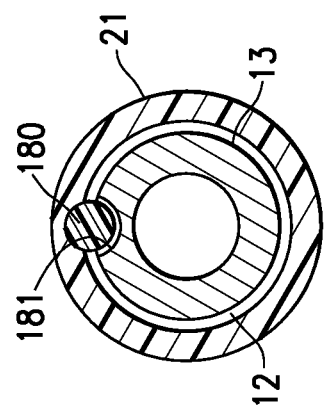
FIG. 30 illustrates a transverse cross sectional view of FIG. 29, taken along line 30-30.

One aspect of the invention is directed to maintaining the needle 13 in a rotational alignment relative to the catheter shaft when the needle is in the retracted or the extended configuration. The needle 13 typically has a beveled sharp distal end, and as a result, the angular orientation of the needle contributes to the ease of tissue penetration during needle advancement. A rotational alignment feature of the invention is generally formed by mating surfaces of the shaft and needle, and is configured to allow for at least some longitudinal movement of the needle while constraining the rotation of the needle relative to the surrounding shaft. FIG. 29 illustrates one embodiment of a rotational alignment feature, generally comprising a protrusion 180 slidingly received in a corresponding recess 181, to thereby maintain the needle in a rotational alignment relative to the shaft in the retracted and in the extended configuration. In the embodiment illustrated in FIG. 29, the recess 181 is a slot in the outer surface of the needle 13 extending partially through the wall of the needle, and the protrusion extends radially inwardly from the inner surface of the needle sheath tubular member 21. The protrusion 180 is preferably an axially extending short length of round wire, typically bonded to the needle sheath tubular member 21 within a void in the wall of the needle sheath tubular member 21. FIG. 29 illustrates a section of the needle sheath tubular member 21 and the wire protrusion 180 in longitudinal cross section, with the slotted section of the needle 13 therein. FIG. 30 illustrates a transverse cross section of FIG. 29, taken along line 30-30.

Figure 31:
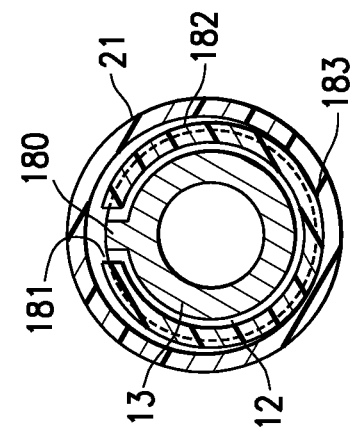
FIG. 31 illustrates a transverse cross sectional view of an alternative embodiment of the rotational alignment feature, in which the needle has an outer protrusion.

The rotational alignment feature can be provided anywhere along the length of the shaft proximal to the needle-through port 14. In the embodiment of FIG. 29 in which the recess 181 is in the wall of the needle 13, the rotational alignment feature is preferably provided along a proximal section of the needle 13 where the needle wall thickness is relatively thick to better accommodate the recess 181 compared to a more distal section of the needle 13. Alternatively, rather than form the recess 181 directly into the outer surface of the needle 13, a guide tube member having the recess 181 formed in an outer surface thereof can be fixedly secured on a section of the needle 13. Additionally, although illustrated with the recess 181 in the needle 13 and the protrusion on the shaft in the embodiment of FIG. 29, in alternative embodiments, the protrusion extends radially outwardly from the needle outer surface and is received in a recess in the inner surface of the needle sheath tubular member 21. For example, FIG. 31 illustrates an embodiment in which the needle 13 is ground to form outwardly extending protrusion 180, and a guide tube member 182 fixedly secured to an inner surface of the needle sheath tubular member 21 has a slit which forms the protrusion-receiving recess 181. The protrusion 180 is preferably formed by removing material from the outer surface of the needle 13, for example by laser etching, along a section of the needle 13. The protrusion 180 outer diameter in the embodiment of FIG.

31 thus aligns with the outer diameter of the needle sections proximally and distally adjacent to the rotational alignment feature (the outer diameter of the adjacent section of the needle is illustrated in dashed lines in FIG. 31, behind the slitted guide tube member 182). The slitted guide tube member 182 is bonded, for example by adhesive or heat fusion bonding, or press fit bonding, to the inner surface of the needle sheath tubular member 21. The guide tube member 182 is bonded around an arc 183 of its circumference opposite to the slit recess 181, in the embodiment of FIG. 31, although it could alternatively be bonded around its entire circumference to the inner surface of the needle sheath tubular member 21. The protrusion 180 or guide tube 182 may span a junction between two sections of the needle sheath tubular member 21, providing support at the junction and ease of manufacturability.

Figure 34:
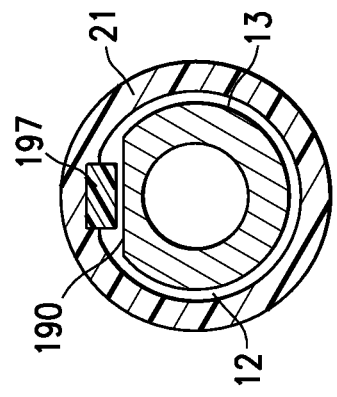
FIG. 34 illustrates a transverse cross sectional view of an embodiment in which the reduced radius portion of the inner circumference of the shaft is a constraint inserted into the shaft and secured to the inner surface of the shaft.
Figure 33:
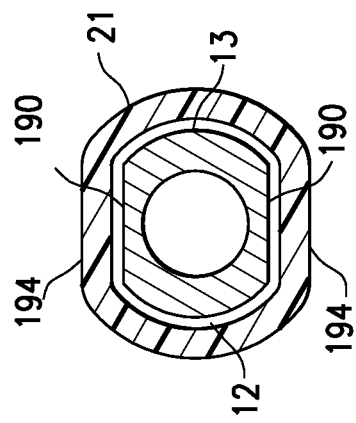
FIG. 33 illustrates a transverse cross sectional view of an embodiment in which the reduced radius portion of the inner circumference of the shaft is a flattened portion of the inner surface of shaft.
Figure 32:
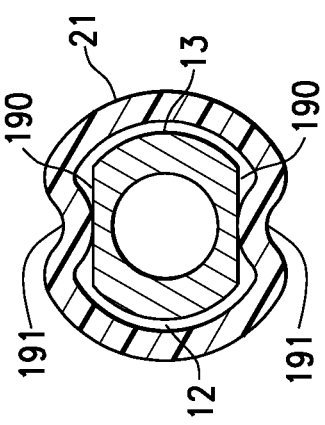
FIG. 32 illustrates a transverse cross sectional view of an alternative embodiment of the rotational alignment feature, in which the needle has a flattened outer surface around a portion of the circumference of the needle configured to stop rotation of the needle in the shaft by contacting a reduced radius portion of the inner circumference of the shaft formed by a depressed wall of the shaft.

FIGS. 32-34 illustrate alternative embodiments in which the rotational alignment feature is formed in part by a flattened outer surface of the needle 13. Specifically, the needle 13 has a circular transverse cross sectional shape with at least a section along which the needle has a flattened outer surface 190 around a portion of the circumference of the needle configured to stop rotation of the needle in the shaft by contacting a reduced radius portion of the inner circumference of the shaft, to thereby maintain the needle in a rotational alignment relative to the shaft in the retracted and in the extended configuration. In the embodiment of FIG. 32, the reduced radius portion of the inner circumference of the shaft is a depression or crease 191 in the wall of the needle sheath tubular member 21. In the illustrated embodiment, the catheter has two creases 191 opposite to one another. The crease 191 can be formed by applying an inward force on the outer surface of the needle sheath tubular member 21 to depress and plastically deform the outer and inner surfaces inwardly. The flattened outer surface 190 of the needle 13 can be formed by a variety of suitable methods including grinding, cutting or otherwise removing material from the outer surface of the cylindrical needle. The needle has at least one, and more preferably two oppositely disposed flattened outer surfaces 190.

FIG. 33 illustrates an alternative embodiment in which the reduced radius portion of the inner circumference of the shaft is flattened inner surfaces 194 around a portion of the circumference of the needle-through lumen 12, circumferentially aligned with the flattened outer surfaces 190 of the needle. FIG. 34 illustrates an alternative embodiment in which the reduced radius portion of the inner circumference of the shaft is a protrusion 147 having a flat surface extending inwardly from the inner surface of the shaft. The protrusion is typically a member bonded in a slot in the inner surface of the needle sheath tubular member 21. Although the reduced radius portions are formed by the inner surface of the needle sheath tubular member 21 in the embodiments of FIGS. 32 and 33, they can alternatively be provided by a tube insert which provides the desired reduced radius shape and which is bonded to an inner surface of the needle sheath tubular member 21. The rotational alignment features of the embodiments of FIGS. 32-34 can extend the proximal length of the needle 13 and needle sheath tubular member 21 such that they do not provide a stop for the longitudinal advancement of the needle 13 in the shaft needle-through lumen 12, or alternatively can be distally adjacent to a proximal section of the needle 13 having a (nonflattened) round outer surface extending continuously around the circumference of the needle that is configured to abut the reduced radius portion of the needle sheath tubular member 21 to act as a stop preventing further longitudinal advancement of the needle.

Figure 35:
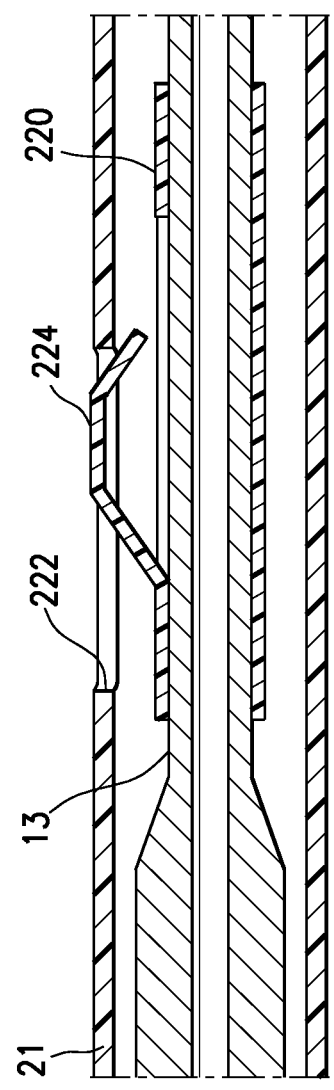
FIG. 35 illustrates an alternative embodiment of the rotational alignment feature, in which an outer protruding member on the needle is constrained in a slot in the needle-sheath tubular member of the catheter.
Figure 36:
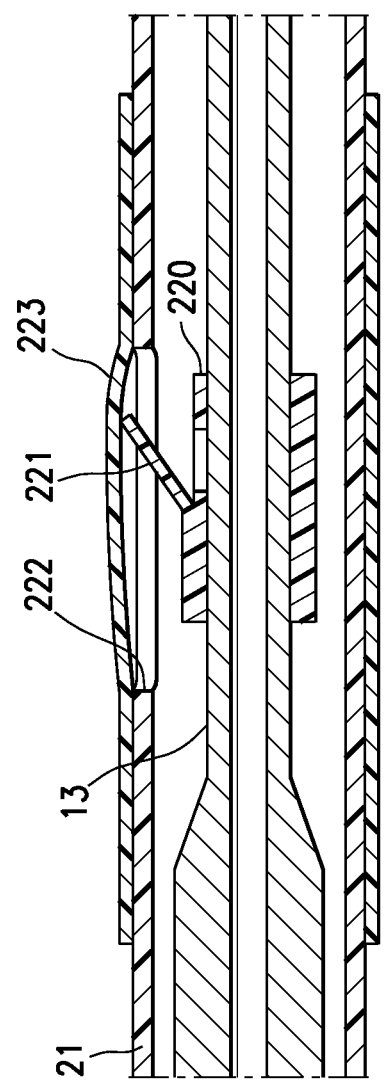
FIG. 36 illustrates an embodiment in which a tab of the outer protruding member is bent radially inwardly toward an outer surface of the needle.

FIG. 35 illustrates a longitudinal cross section of an alternative embodiment of the rotational alignment feature, in which an outer protruding member on the needle is constrained in a slot in the outer surrounding member of the shaft (e.g., the needle-sheath tubular member 21) to thus permit axial movement, while limiting rotation movement, of the needle relative to the shaft. Specifically, a guide protruding tube 200 is secured to an outer surface of the needle 13 and has a tab 201 extending radially outward from the tube and needle axis. The tab 201 fits within a slot 202 in the wall of the needle-sheath tubular member 21 such that interference contact between the tab 201 and the wall surfaces defining the slot 202 limits the distal axial (longitudinal) advancement of the needle and the rotation of the needle in the shaft. In the embodiment of FIG. 35, a cover 203 over the slot 202 is secured to the needle-sheath tubular member 21, to thereby prevent the tab 201 from catching or otherwise interacting with outer surrounding surfaces such as the patient's surrounding anatomy. The cover 203 has a tubular shape in the illustrated embodiment, and is typically a polymeric material such as polyimide or nylon, to facilitate providing the cover 203 with a sufficiently small profile to maintain the low profile and high flexibility of the shaft. The cover 203 is secured to the needle-sheath tubular member 21 using an interference fit, or an additional or alternative mechanical or chemical bond such as an adhesive bond. The cover 203 is preferably sealingly secured to needle-sheath tubular member 21 to prevent the flow of fluid from the patient's vessel through the slot 202. Although illustrated with cover 203 over the slot 202, it should be understood that the protruding tube 200 of FIG. 35 and alternative embodiments can be used without the cover 203. FIG. 36 illustrates an alternative embodiment, in which the protruding guide tube 200 has a tab 204 bent radially inward toward an outer surface of the needle, to prevent or inhibit the catching-type interactions of the protruding tab (e.g., to protect the surrounding anatomy from the movement of the tab), while still providing a sufficient profile for interference contact in the slot 202 in the needle-sheath tubular member 21 to thereby constrain the needle rotation and distance of axial movement.

The tab 201/204 is preferably formed by cutting, e.g., using laser, micro-machining, or other fine material removal technology, the wall of the tube 200, and plastically deforming (i.e., bending) the wall at the base of the tab, so that the tab extends outward. As a result, the tab is formed from the wall of the tube 200 as an integral, one-piece member, and provides for ease of manufacture. The slot 202 is also typically formed by cutting the wall of the needle-sheath tubular member 21, and in one embodiment has a relatively narrow width sized to substantially correspond to the width of the tab 201/204 with minimal but sufficient clearance to allow movement of the tab in the slot. In the illustrated embodiments, the protruding tube 200 is on a smaller diameter distal section of the needle, spaced a relatively short distance distally from the larger diameter proximal section of the needle. The slot 202 in the needle-sheath tubular member 21 is proximal to the needle-through port 14 but at least in one embodiment is spaced a relatively large distance distally from the proximal end of the shaft. The protruding tube 200 and slot 202 can be located at a variety of suitable locations along the needle-sheath tubular member 21.

The rotational alignment features can alternatively be adapted to be used to provide for rotational alignment of other slidably disposed tubular members of the catheters of the invention, for example to provide for alignment of the needle-through port 14 of the needle sheath tubular member 21 with a side wall port in the shaft inner tubular member.

A variety of suitable agents can be delivered using a catheter and method of the invention. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. Suitable therapeutic agents include, but are not limited to, thrombolytic drugs, anti-inflammatory drugs, anti-proliferative drugs, drugs restoring and/or preserving endothelial function, and the like. A variety of bioactive agents can be used including but not limited to peptides, proteins, oligonucleotides, cells, and the like. The agent is typically a therapeutic agent for restenosis, although the agent can be delivered for a variety of treatment procedures, including treatment of a diseased (occluded) blood vessel by delivery of the agent directly to the diseased blood vessel, or treatment of the myocardium of the heart by delivery of an agent to one of the (healthy) coronary arteries. In a presently preferred embodiment, the agent is an anti-inflammatory agent including steroids, or is an agent that induces cholesterol efflux from arterial wall plaque including ApoA1 mimetic peptides, PPARα agonists. In one embodiment, the catheter is used to deliver an agent into organ tissue, such as renal, spleen, liver, or stomach tissue, or any body organ with vasculature that runs near a target treatment site. The agent(s) can be delivered directly into the organ tissue adjacent to a disease. Suitable agents include anti-proliferative, anti-inflammatory, anti-neoplastic, anti-platelet, anti-coagulant, anti-fibrin, anti-thrombotic, anti-mitotic, antibiotic, anti-allergic, and antioxidant compounds. For example, in one embodiment, the catheter is used to deliver therapeutic agent microparticles into renal tissue. Modifications to the catheter device components may be required to produce a device that operates within different organ vascular systems, for example by reducing or enlarging the size of the device for use in body lumens that are smaller or larger relative to typical coronary vessels. In addition to therapeutic agents, a variety of diagnostic agents can be used according to the present invention. The agent may be provided in a variety of suitable formulations and carriers including liposomes, polymerosomes, nanoparticles, microparticles, lipid/polymer micelles, and complexes of agents with lipid and/or polymers, and the like.

The dimensions of catheters 10, 60, 80, 90, 120 depend upon factors such as the catheter type, and the size of the artery or other body lumen through which the catheter must pass. Typically, for coronary arteries, the expandable members radially expand to a maximum outer diameter of about 3.5 to about 4.5 mm. The overall length of the catheter may range from about 100 to about 130 cm, and is typically about 143 cm.

The needle sheath tubular member 21 is preferably formed of metal such as a nickel-titanium alloy (NiTi) and/or stainless steel, although it can alternatively or additionally be formed of suitable plastics commonly used in catheter shaft construction such as polyamides, polyurethanes, silicone modified polyurethanes, fluoropolymers, polyolefins, polyimides. In one embodiment, the needle sheath tubular member 21 has a proximal section of stainless steel joined to a distal section of NITINOL. In one embodiment the needle 13 has a distal section of NiTi joined to a proximal section of stainless steel, although the needle can alternatively be formed of a single material/tubular member.

The shaft tubular members can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. A variety of suitable shaft configurations can be used including one or more of the tubular members formed of single or multiple layers or sections of tubing, as are conventionally known for catheter shaft design Although discussed primarily in terms of catheters in which the needle extends from within needle sheath tubular member, catheters having the expandable support member(s) in accordance with the invention can have a variety of suitable shaft designs. Additionally, the term "catheter" should be understood to refer to a variety of device designs generally having an elongated structure configured for percutaneous advancement through a patient's vasculature. While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. An agent delivery catheter configured for delivering an agent to an injection site in a wall of a patient's body lumen, comprising:
    a) an elongated shaft having a lumen for receiving a tubular member defining a needle-through lumen therein extending from the proximal end of the tubular member to a needle-through port in a side of a distal section of the tubular member, and a needle slidably disposed in the needle-through lumen having a retracted configuration and an extended configuration in which the needle extends laterally from the tubular member through the needle-through port and through an opening in the elongated shaft; and
    b) a radially-self expanding open-walled frame on the distal section of the shaft tubular member, the frame including a plurality of longitudinally extending struts, each strut having a first end fixedly secured to the shaft tubular member and a free opposite second end, the frame having a collapsed configuration, and a radially expanded configuration in which the free ends of the frame expand radially outward into contact with the body lumen wall, and which extends around the circumference and along an outer surface of the shaft tubular member to substantially center the shaft tubular member distal section at the location of the port in the body lumen in the expanded configuration, such that the expandable frame in the expanded configuration supports the shaft tubular member in a position spaced away from the body lumen wall around the circumference of the shaft tubular member at the location of the port, and the needle slidably exits the needle-through lumen in the extended configuration through the port spaced away from the body lumen wall as the expandable frame supports the shaft tubular member at the port.

2. The catheter of claim 1 wherein the shaft tubular member is metallic, and the catheter includes an outer sheath slidably disposed on the frame in an advanced configuration surrounding the frame to constrain the frame in a collapsed configuration, and having a retracted configuration which allows the frame to radially self-expand.

3. The catheter of claim 1 wherein the expandable frame includes a plurality of slots which align with the opening on the elongated shaft to allow the needle to slidably exit the needle-through lumen and shaft when the frame is in the expanded configuration and the needle is in the extended position.

4. The catheter of claim 3 wherein the expandable frame includes an non-expandable tubular section which is disposed on the outer shaft, the plurality of slots extending through the non-expandable tubular section.

5. The catheter of claim 3 wherein the slots extend longitudinally along the length of the shaft.

6. The catheter of claim 1 wherein the tubular member is sliding disposed within the lumen of the shaft.

7. The catheter of claim 1 wherein the tubular member is rotatable within the lumen of the shaft.

8. The catheter of claim 1 wherein the dimension of one or more of the struts varies along the length of the strut, so that the level of support that the frame provides to the catheter shaft varies along the length thereof.

9. The catheter of claim 1 wherein the shaft and needle include a rotational alignment feature formed by mating surfaces of the shaft and needle, comprising a protrusion slidably received in a corresponding recess of an adjacent surface, to thereby maintain the needle in a rotational alignment relative to the shaft in the retracted and in the extended configuration.

10. The catheter of claim 1 wherein the needle has a circular transverse cross sectional shape with at least a section along which the needle has a flattened outer surface around a portion of the circumference of the needle configured to stop rotation of the needle in the shaft by contacting a reduced radius portion of the inner circumference of the shaft, to thereby maintain the needle in a rotational alignment relative to the shaft in the retracted and in the extended configuration.

* * * * *